US012721610B2

(12) United States Patent
Major et al.

(10) Patent No.: US 12,721,610 B2
(45) Date of Patent: Sep. 1, 2026

(54) ELONGATE FLEXIBLE SYSTEMS WITH ARTICULATION JOINT ASSEMBLY

(71) Applicant: INTUITIVE SURGICAL OPERATIONS, INC., Sunnyvale, CA (US)

(72) Inventors: Christopher M. Major, Santa Clara, CA (US); Joseph D. Bogusky, San Jose, CA (US); Lucas S. Gordon, San Jose, CA (US); Francis T. Macnamara, San Jose, CA (US); Randall L. Schlesinger, San Mateo, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 453 days.

(21) Appl. No.: 17/972,415

(22) Filed: Oct. 24, 2022

(65) Prior Publication Data

US 2023/0128263 A1 Apr. 27, 2023

Related U.S. Application Data

(60) Provisional application No. 63/271,317, filed on Oct. 25, 2021.

(51) Int. Cl.
*A61B 1/00* (2006.01)
*A61B 17/00* (2006.01)
(Continued)

(52) U.S. Cl.
CPC .................. *A61B 17/00234* (2013.01); *A61B 2017/00314* (2013.01); *A61B 2017/00327* (2013.01);
(Continued)

(58) Field of Classification Search
CPC .......... A61B 17/00234; A61B 17/0055; A61B 17/0051; A61B 17/008;
(Continued)

(56) References Cited

U.S. PATENT DOCUMENTS 6,672,338 B1 * 1/2004 Esashi ............... A61M 25/0138 138/119
8,475,366 B2 7/2013 Boulais et al.
(Continued)

OTHER PUBLICATIONS

Contiguous definition, Merriam-Webster online, https://web.archive.org/web/20180710103603/https://www.merriam-webster.com/dictionary/contiguous (Year: 2018).*
(Continued)

*Primary Examiner* — Anh Tuan T Nguyen
*Assistant Examiner* — James Edward Boice
(74) *Attorney, Agent, or Firm* — Haynes & Boone, LLP.

(57) ABSTRACT

A catheter system may comprise an articulation joint including a first pair of links and a second pair of links. Each link may include a central channel enclosed at least in part by radially extending arcuate segments. The first pair of links may include a first link and a second link, and the second pair of links may include the second link and a third link. The system may also comprise a first pair of springs coupled between the first and second links. The system may also comprise a second pair of springs coupled between the second and third links. The system may also include control wires extending through the first pair of springs and a control wires extending through the second pair of springs. The spring walls may share a radial dimension with the link walls.

24 Claims, 15 Drawing Sheets

(51) Int. Cl.
*A61M 25/00* (2006.01)
*A61M 25/01* (2006.01)

(52) U.S. Cl.
CPC .............. *A61B 2017/00336* (2013.01); *A61M 2025/0004* (2013.01); *A61M 25/0138* (2013.01)

(58) Field of Classification Search
CPC ...... A61B 2017/00309; A61B 1/00078; A61B 1/00–32; A61B 2017/00331; A61M 17/00234; A61M 17/00314; A61M 17/00327; A61M 17/00336; A61M 25/0138; A61M 2025/0004; A61M 25/01; A61M 25/0102
USPC .... 600/146, 141; 604/214, 164.11, 264, 604
See application file for complete search history.

(56) References Cited

U.S. PATENT DOCUMENTS

2005/0075538 A1* 4/2005 Banik .................. A61B 1/0052 600/152
2005/0131279 A1* 6/2005 Boulais ................ A61B 1/0016 600/141
2005/0272975 A1* 12/2005 McWeeney ............ A61B 1/307 600/172
2007/0255105 A1* 11/2007 Ochi .................... A61B 1/0055 600/153
2007/0270752 A1* 11/2007 LaBombard ....... A61B 1/00154 604/164.01
2008/0286036 A1* 11/2008 Macnamara ......... A61B 1/0055 29/896.9
2015/0359416 A1* 12/2015 Simchony ............ A61B 1/0055 600/110
2022/0126060 A1* 4/2022 Shia .................. A61M 25/0009
2023/0083702 A1* 3/2023 Lau ................... A61M 25/0009 219/121.63

OTHER PUBLICATIONS

Noncontiguous definition, Merriam-Webster online, https://web.archive.org/web/20191215072148/https://www.merriam-webster.com/dictionary/noncontiguous (Year: 2019).*
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

ELONGATE FLEXIBLE SYSTEMS WITH ARTICULATION JOINT ASSEMBLY

CROSS-REFERENCED APPLICATIONS

This application claims priority to and benefit of U.S. Provisional Application No. 63/271,317, filed Oct. 25, 2021 and entitled "Elongate Flexible Systems with Articulation Joint Assembly," which is incorporated by reference herein in its entirety.

FIELD

Examples described herein relate to elongate flexible systems, such as catheter systems, with articulation joint assemblies that may incorporate spring members and links that provide axial stiffness and bending flexibility in a low-profile design.

BACKGROUND

Minimally invasive medical techniques are intended to reduce the amount of tissue that is damaged during interventional procedures, thereby reducing patient recovery time, discomfort, and harmful side effects. Such minimally invasive techniques may be performed through natural orifices in a patient anatomy or through one or more surgical incisions. Physicians may insert minimally invasive medical instruments (including surgical, diagnostic, therapeutic, or biopsy instruments) through these natural orifices or incisions to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device.

Various parameters may be considered in the design of elongate flexible systems. For example, a relatively high axial stiffness may reduce compression along the longitudinal axis, but a relatively low bending stiffness may allow the device to flexibly navigate anatomical passageways. A relatively large central channel may allow for passage of a variety of instruments through the elongate flexible device, but a relatively small outer diameter may allow the system greater access to narrow anatomical passageways. Elongate flexible devices, such as catheters, are needed that may optimize these and/or other design parameters.

SUMMARY

The following presents a simplified summary of various examples described herein and is not intended to identify key or critical elements or to delineate the scope of the claims.

In some examples, a catheter system may comprise an articulation joint including a first pair of links and a second pair of links. Each link may include a central channel enclosed at least in part by radially extending arcuate segments. The first pair of links may include a first link and a second link, and the second pair of links may include the second link and a third link. The system may also comprise a first pair of springs coupled between the first and second links and extending between a pair of the arcuate segments of the first link and a first pair of the arcuate segments of the second link. The system may also comprise a second pair of springs coupled between the second and third links and extending between a second pair of the arcuate segments of the second link and a pair of the arcuate segments of the third link. The second pair of springs may be offset in angular position from the first pair of springs. The system may also include a first pair of control wires extending through the first pair of springs and a second pair of control wires extending through the second pair of springs. At least one spring of the first pair of springs may have a spring wall, and the first link may have a link wall. The spring wall may share a radial dimension with the link wall.

In some examples, a catheter system may comprise an articulation joint including a pair of links including a first link and a second link and a spring coupled between a first pair of spaced apart segments of the first link and between a first pair of spaced apart arcuate segments of the second link. The spring may be bendable to allow articulation of the pair of links along a first plane of motion. The system may also include a control wire extending through the spring.

In some examples, a catheter system comprises an articulation joint including first and second links, each link including an inner wall. A plurality of grooves may extend axially along the inner wall of each of the first and second links. The system may also comprise a pair of springs coupled between the first and second links, the pair of springs may be bendable to allow articulation of the first and second links along a first plane. Each spring of the pair of springs is coupled to a respective one of the plurality of grooves of the first link and coupled to a respective one of the plurality of grooves of the second link. The system may also include a plurality of control wires. A respective one of the plurality of control wires extends through each of the springs of the pair of springs.

In some examples, a catheter system may comprise an articulation joint including a pair of links. Each link may include a central channel and a pair of conduits extending in a wall of the link. The system may also include a pair of springs coupled between the pair of links. The pair of springs may be bendable to allow articulation of the pair of links along a first plane. Each spring of the pair of springs may be axially aligned with a respective conduit of the pair of conduits. The system may also include a respective control wire extending through each of the springs of the pair of springs.

In some examples, a catheter system may comprise an articulation joint including first and second links, each link including a central channel. The system may also include a pair of springs coupled between the first and second links. The pair of springs may be bendable to allow articulation of the first and second links along a first plane. Each spring of the pair of springs may be incorporated in a wall of a first link and in a wall of the second link. The system may also include a coil extending between the first and second links. The coil may be axially aligned with the central channel. The system may also include a respective control wire extending through each of the springs of the pair of springs.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
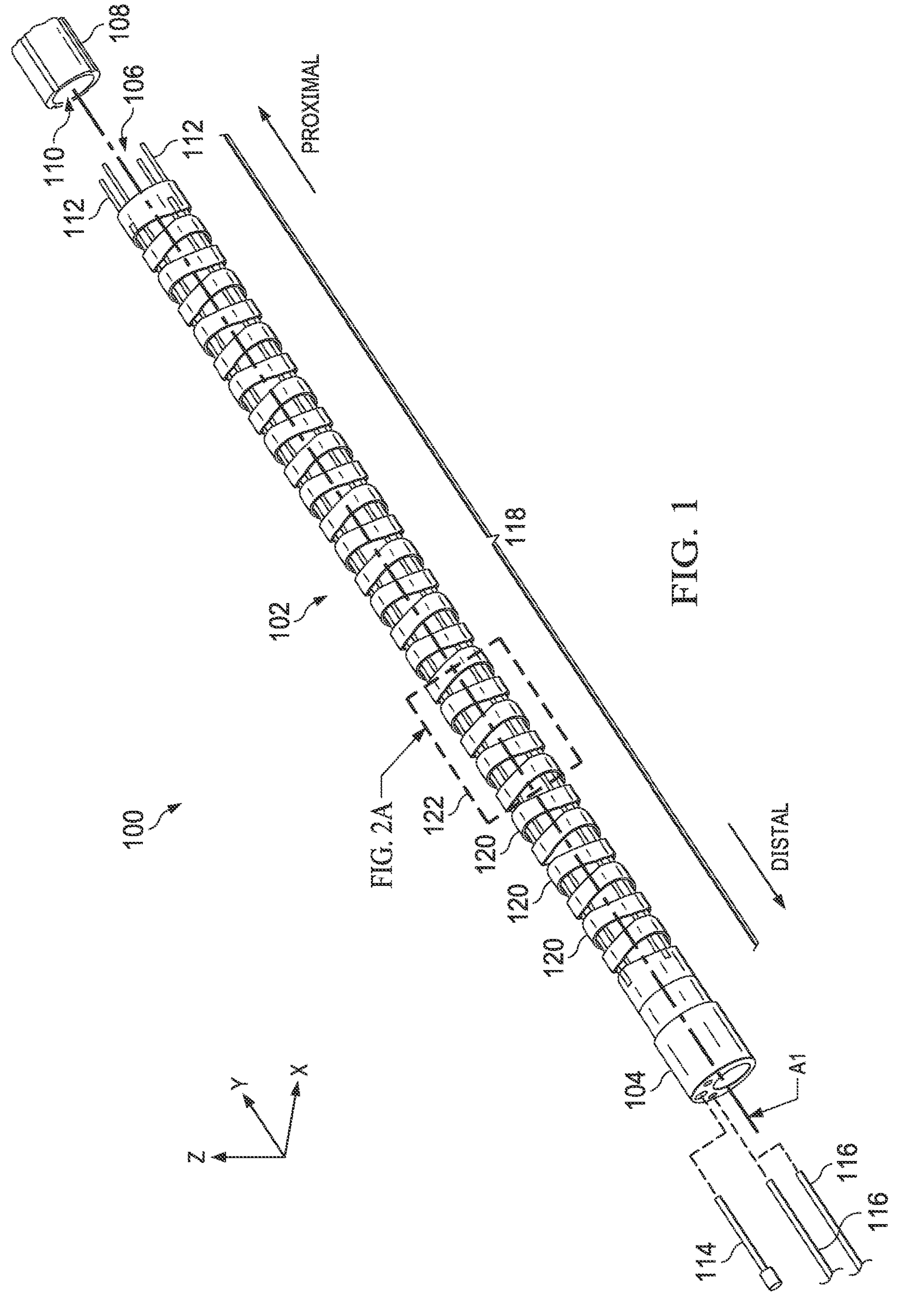
FIG. 1 illustrates an exploded view of an elongate flexible device including an articulation joint according to some examples.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

FIG. 1 illustrates an exploded view of an elongate flexible device 100 having a device frame of reference having a coordinate system X,Y,Z. In some examples, the elongate flexible device 100 may be an elongate device, such as a catheter, of a medical instrument system. The elongate flexible device 100 may include an articulation portion 102 coupled to a distal mount 104. A central passage or channel 106 may extend through the articulation portion 102, and a liner 108 may extend within the central channel 106. The liner 108 may form a lumen 110. The lumen 110 may provide a delivery channel for a medical tool (not shown), such as an endoscope, biopsy needle, endobronchial ultrasound (EBUS) probe, ablation tool, chemical delivery tool, and/or the like, to be inserted through elongate flexible device 100.

A set 112 of actuation members may extend through the articulation portion 102 terminating at a distal section of the articulation portion 102 or at the distal mount 104. The set 112 of actuation members may be arranged circumferentially about a longitudinal axis A1 through the device 100. An imaging device 114 and one or more peripheral systems such as lighting members 116 may extend through the articulation portion 102 and may terminate or extend from the distal mount 104. In some examples, various other types of components such as electrical wires, fibers, sensors, small medical instruments, fluid delivery conduit, suction conduit, chemical delivery conduit, and/or the like may also or alternatively extend through the articulation portion 102.

The articulation portion 102 may be configured to bend in response to actuation forces applied by the set 112 of actuation members. The articulation portion 102 may include a support structure 118 to prevent or reduce distortion, compression and/or collapse under axial loads. The support structure 118 may have an axial stiffness that supports the articulation portion 102 against axial loads generated by the actuation forces applied to the set 112 of actuation members and by axial forces generated by contact with surrounding anatomical tissue. The higher the axial stiffness of the support structure 118 is, the more resistant the support structure 118 may be to compression or buckling under heavy axial load. A higher axial stiffness also increases the controls responsiveness and predictiveness. The support structure 118 also has a bending stiffness that resists bending of the articulation portion 102. The lower the bending stiffness of the support structure 118 is, the more flexible and bendable the support structure 118 may be in response to bending forces applied by the set 112 of actuation members. A lower bending stiffness in the support structure 118 may allow the set 112 of actuation members to steer the articulation portion 102 with lower forces.

Figure 2A:
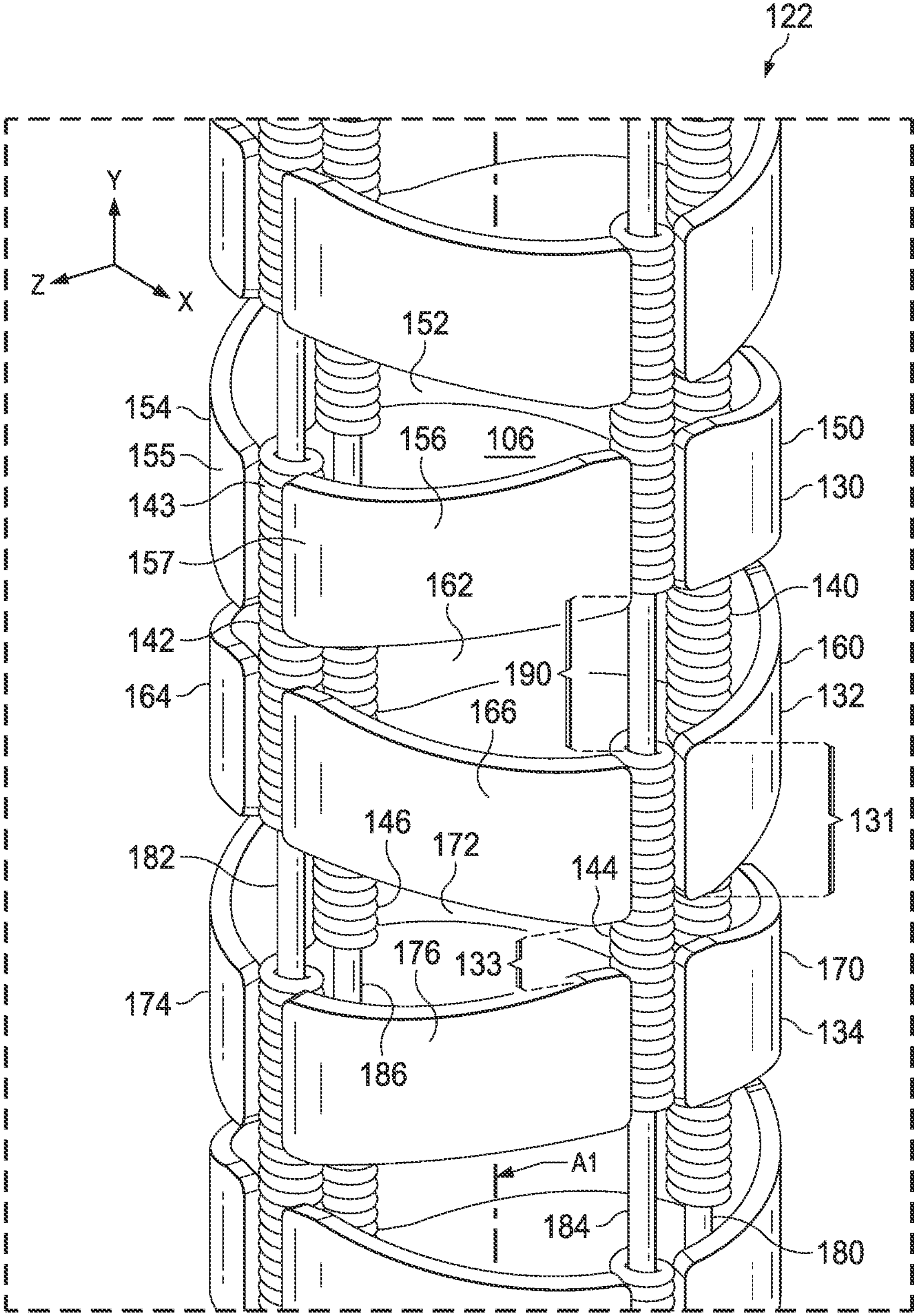
FIG. 2A illustrates a portion of the articulation joint of FIG. 1 in an unbent configuration, according to some examples.
Figure 2B:
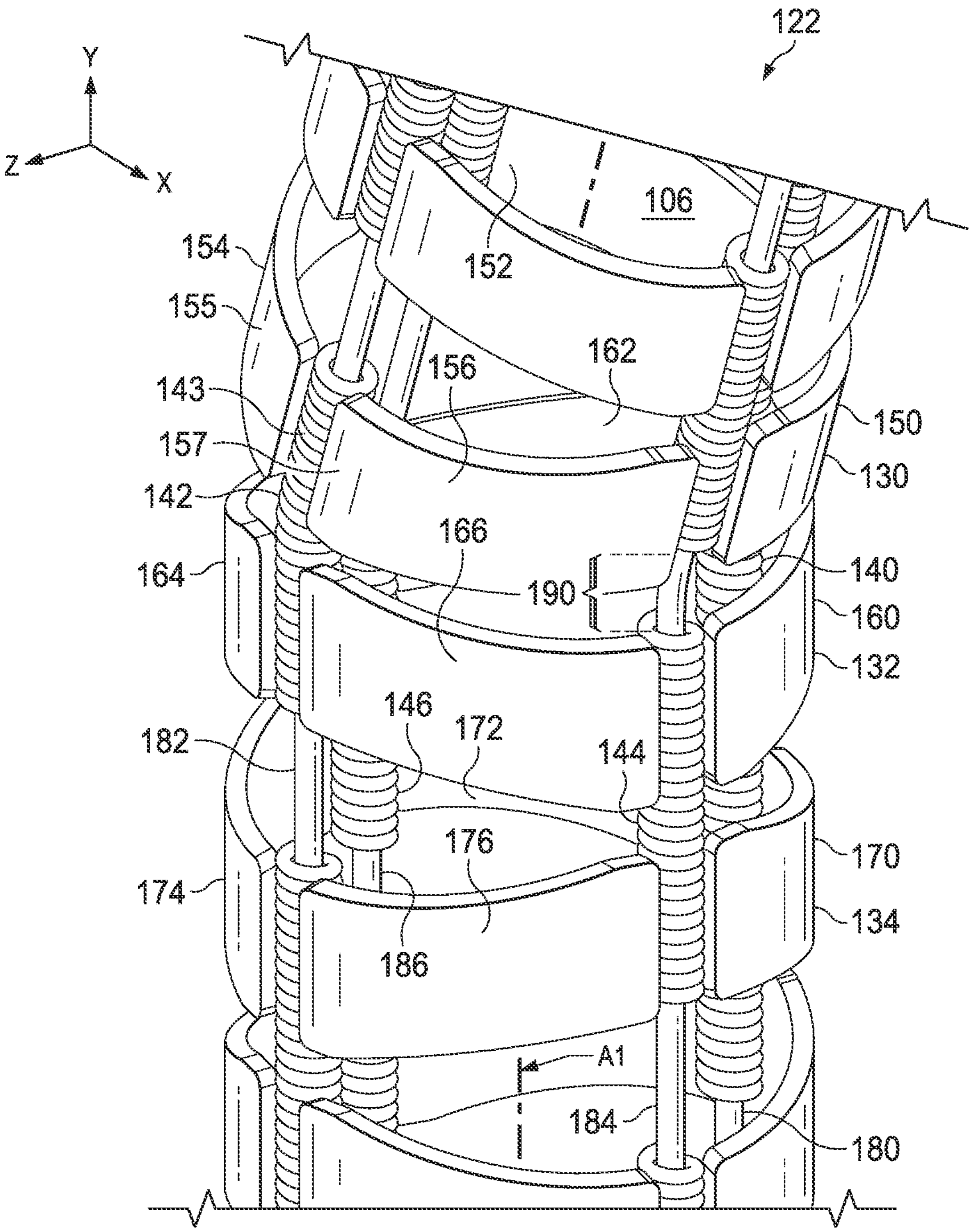
FIG. 2B illustrates a portion of the articulation joint of FIG. 1 bent in a first plane.
Figure 2C:
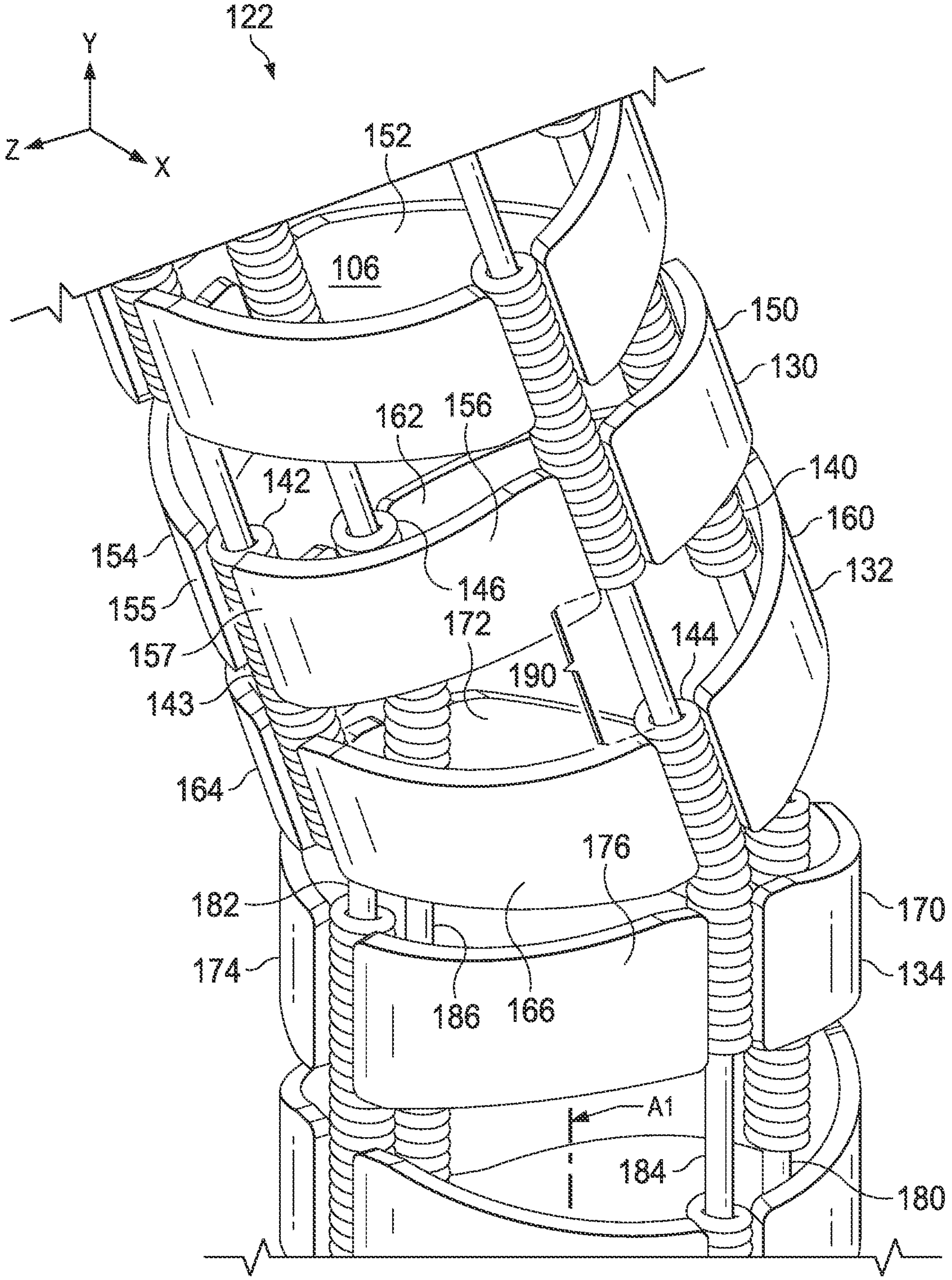
FIG. 2C illustrates a portion of the articulation joint of FIG. 1 bent in a second plane.

The support structure 118 may include a series of links 120 forming a spine-like structure. FIG. 2A illustrates an articulation joint 122 of the articulation portion 102, including the support structure 118, in an unbent configuration. The articulation joint 122 includes link 130 (e.g., a first link), link 132 (e.g., a second link), and link 134 (e.g., a third link), of the series of links 120, arranged in series along the axis A1. The articulation joint 122 also includes paired spring members 140, 142 extending between paired links 130, 132 and paired spring members 144, 146 extending between paired links 132, 134. As shown in FIG. 2B, the paired spring members 140, 142 and the paired links 130, 132 may allow bending of the articulation joint 122 in a first plane (e.g., plane XY). As shown in FIG. 2C, the paired spring members 144, 146 and the paired links 132, 134 may allow bending of the articulation joint 122 in a second plane (e.g., plane YZ). The first and second planes may be perpendicular to each other. As shown in FIG. 2A-2C, a link (e.g., link 132) of an articulation joint may be a member of a first paired set of links (e.g., pair 130, 132) while also being a member of a second paired set of links (e.g., pair 132, 134). In this example, the paired spring members 140, 142 may be positioned at an angular offset of approximately 90 degrees from the paired spring members 144, 146.

Each link of the articulation joint 122 may be circumferentially non-contiguous including spaced-apart, radially extending arcuate segments between which a spring member is coupled. For example, link 130 may include arcuate segments 150, 152, 154, 156 separated and arranged radially about axis A1. Link 132 may include arcuate segments 160, 162, 164, 166. Link 134 may include arcuate segments 170, 172, 174, 176. An upper portion of the spring member 140 may be coupled between segments 150, 152 and a lower portion of the spring member 140 may be coupled between segments 160, 162. An upper portion of the spring member 142 may be coupled between segments 154, 156 and a lower portion of the spring member 142 may be coupled between segments 164, 166. An upper portion of the spring member 144 may be coupled between segments 160, 166 and a lower portion of the spring member 144 may be coupled between segments 170, 176. An upper portion of the spring member 146 may be coupled between segments 162, 164 and a lower portion of the spring member 146 may be coupled between segments 172, 174. The spring members may be coupled to the respective segments by laser welding and/or by any other type of physical or adhesive coupling. In some examples, the spring members might not extend distally or proximally beyond the links to which they are coupled. For example, the spring member 144 may terminate at approximately a distal edge of the link 134 and at approximately a proximal edge of the link 132. In some examples the spring members may terminate before the distal edge of the link and before the proximal edge of the link. To span a gap 133 between the links 132, 134, the spring member 144 may have a length that is equal to or greater than a proximal to distal height 131 of any one link.

In some examples, the arcuate sections may have approximately equal arcuate lengths such that the spring members may be evenly spaced around the circumference of the device 100. In other examples, one or more of the arcuate sections may have different arcuate lengths, thus varying the circumferential arrangement of the spring members. Although the example of FIGS. 2A-2C depict links each with four arcuate sections coupled to four spring members, in other examples, more or fewer arcuate sections and spring members may be used.

The support structure 118 may be formed, for example, from a metal tube, a shape-memory material tube, or a polymer tube. For example, the support structure may be formed from a stainless steel hypotube machined or otherwise cut to form the described links. In other examples, the support structure may be formed from a nitinol hypotube. Other materials that have a high axial stiffness (e.g., resistant to compression) and a low bending stiffness (e.g., high flexibility) may be used to form the support structure. The support structure may also be formed from a flat sheet of suitable material such as stainless steel and then rolled and potentially welded along the seam line to form the tubular structure.

The set 112 of actuation members includes an articulation member 180 that may extend through the spring member 140, an articulation member 182 that extends through the spring member 142, an articulation member 184 that extends through the spring member 144, and an articulation member 186 that extends through the spring member 146. The articulation members 180, 182, 184, 186 may further extend through additional spring members in articulation joints located distally and proximally of the articulation joint 122. The spring members may be open-pitch coiled springs, closed-pitch coils (e.g., coil pipe of a Bowden cable), flexible conduit, laser cut hypotube, or other tubular structures that are bendable and biased to elastically return from a bent configuration to a straightened configuration in the absence of a bending force. In some examples, an open-pitch coil may allow for more complex bend patterns or more complex navigation maneuvers, such as inch-worm type motion using combination movements of articulation members. The spring members include central passages through which the articulation members may extend. The articulation members may include control wires, tendons, push rods and/or the like. The articulation members may extend out of their respective spring members at bending gaps between links. For example, the articulation member 184 extends proximally beyond the spring member 144 across a bending gap 190 between the links 132 and 130. The gaps between the links may be uniform or may vary in width along the length of the articulation joint to more specifically control the bend radius along the length. One or more of the articulation members 180, 182, 184, 186 may be used to actuate the articulation joint 122. The bend angle that may be achieved between paired links may be based on the geometry of the link. For example, the cut angle at the distal end of link 130 and the cut angle at the proximal end of link 132 may determine the bending gap 190 and may determine the amount of bend angle that can be achieved between these two links when the articulation members 180, 182, 184, 186 are actuated. If a smaller bending radius is desired on articulation joint 122, the height of each link may be reduced and/or the bending gap 190 may be increased. If a larger bending radius is desired on articulation joint 122, the height of each link may be increased and/or the bending gap 190 between each link may be decreased.

In some examples, an articulation joint may have fewer than or more than two pairs of spring members and fewer or more than two sets of links. In some examples, an articulation joint may have fewer or more than two pairs of articulation members. In some examples, the offset between the pairs of spring members may be greater than or less than 90 degrees As shown in FIG. 2B, movement of the articulation members 184, 186 may cause the paired spring members 140, 142 to bend, allowing the paired links 130, 132 to move with respect to each other to allow bending of the articulation joint 122 in the first plane (e.g., plane XY). The paired spring members 140, 142 in both a bent configuration and straight configuration also provide guided passage for the articulation members 180, 182. As shown in FIG. 2C, articulation of the articulation members 180, 182 may cause the paired spring members 144, 146 to bend, allowing the paired links 132, 134 to move with respect to each other to allow bending of the articulation joint 122 in the second plane (e.g., plane YZ). The paired spring members 144, 146, in both a bent configuration and in a straight configuration, provide guided passage for the articulation members 184, 186.

Figure 6:
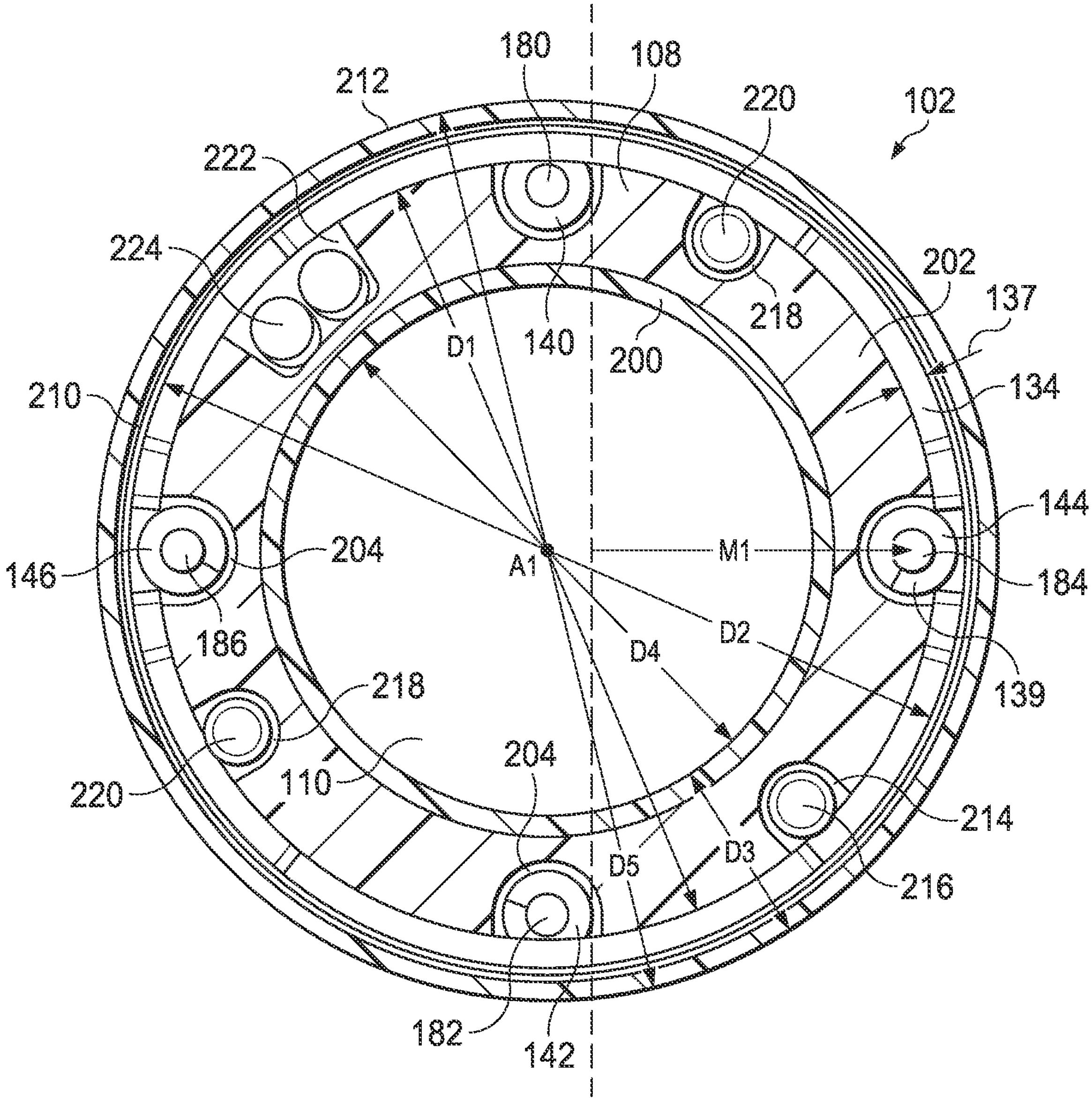
FIG. 6 illustrates a cross-sectional view of the catheter system of FIG. 5.

The spring members may each have a spring wall that shares a same radial dimension as a link wall. With reference to FIG. 6, for example, the wall of link 134 may have a radial dimension 137 (e.g., a spatial ring spanning the distance between the inner and outer surfaces of the link 134), and at least a portion of the wall 139 of spring member 144 shares or extends within the radial dimension 137. In some examples an entire thickness of the spring wall may be within the radial dimension 137, and in other examples, less than the entire thickness of the spring wall (e.g., approximately 70%) may be within the radial dimension with the remainder extending into the interior of the link. In some examples, the wall of the spring member may be tangential to the link wall. For example as shown in FIGS. 2A-2C, the spring members may have an outer surface tangential to or recessed from an outer surface of the adjacent arcuate segments. For example, an outer surface of the spring member 142 may have an outer surface 143 that is tangential to or recessed from the outer surface 155 of segment 154 and the outer surface 157 of segment 156. In other words, the spring member 142 may be entirely within a region bounded by an outer diameter of the link 130. Similarly, the other spring members in the articulation joint 122 may be tangential to or recessed within the outer diameter of the links in which they are coupled. As compared to other designs in which link members are circumferentially continuous and have conduits for articulation members that are either entirely interior to the link, exterior to the link, or positioned in grooves in the link, the configuration of articulation portion 102 with the spring members coupled between discontinuous arcuate segments of the links may allow for a smaller overall cross-sectional wall dimension (e.g., distance between the inner surface of the liner and the outer surface of the link).

Figure 3A:
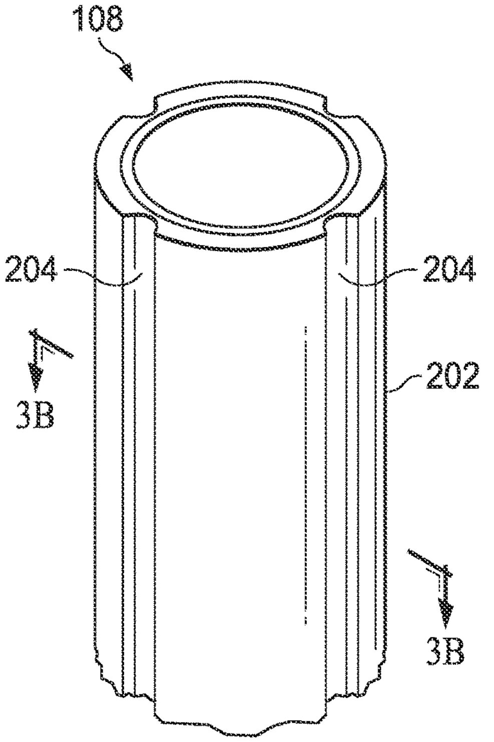
FIG. 3A illustrates a catheter liner for use with an articulation joint according to some examples.
Figure 3B:
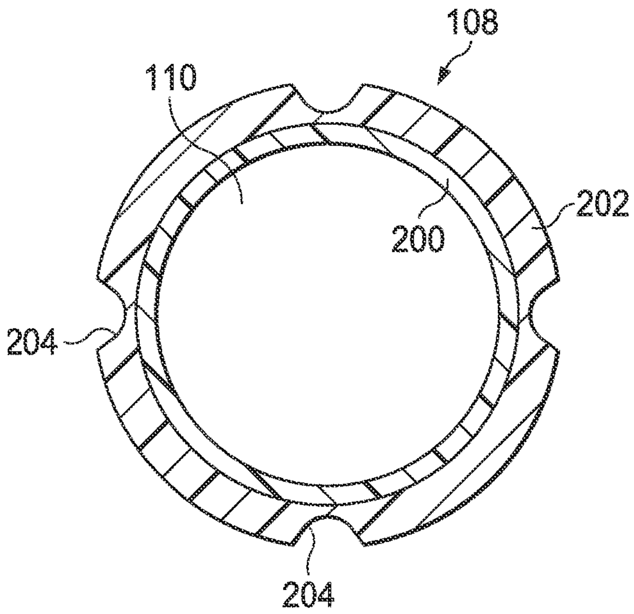
FIG. 3B illustrates a cross-sectional view of the catheter liner of FIG. 3A.

FIGS. 3A and 3B illustrate a flexible tubular liner 108 which may extend within the central channel 106 of the articulation portion 102. The liner 108 defines the lumen 110 which may form a working channel for the smooth, slidable passage of instruments or other systems through the articulation portion 102. As shown in the cross-sectional view of FIG. 3B, the liner 108 may include an inner layer 200 formed of a polymer or other material that may withstand repeated cleaning and may be relatively non-porous and resistant to penetration by fluids or other chemicals that may pass through the lumen 110. In some examples, the layer 200 may be formed of polytetrafluoroethylene (PTFE). The liner 108 may also include an outer layer 202 formed of a polymer or other material that may be conducive to the formation of grooves 204 to accommodate the spring members 140, 142, 144, 146 extending within the central channel 106 of the articulation portion 102. The material may be sensitive to temperature, allowing the grooves 204 to be formed by being drawn through a heated fixture that forms the grooves in the outer surface of the outer layer 202. In some examples, the layer 202 may be formed from expanded polytetrafluoroethylene (ePTFE). The thickness of the liner wall may be thinner at the grooves 204 to accommodate the spring members protruding into the central channel 106 but otherwise allowing a robust wall thickness that allows for repeated use and cleaning. In some examples, the grooves 204 may be spaced at approximately 90 degree increments about the circumference of the outer layer to accommodate the spring members, but in other examples the grooves may be located in different radial positions to accommodate a different spacing of the spring members or other components extending within the central channel 106 of the articulation portion 102. Additional grooves may be formed to accommodate components such as a fiber optic shape sensor, an imaging system, an illumination system, an irrigation system, or other systems that extend through the articulation portion 102 to perform or support a procedure performed with the flexible device 100. The grooves in the outer layer may allow the components and/or the spring members to slide with minimal friction against the liner 108. Although the liner may have two layers as described, in other examples, a liner may be a single layer or may include more than two layers.

Figure 4:
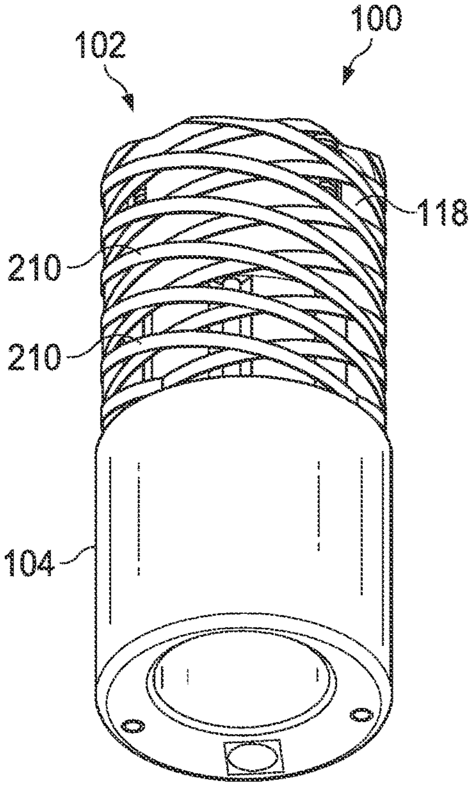
FIG. 4 illustrates a distal end of an elongated flexible device according to some examples.

FIG. 4 illustrates a distal end of the elongate flexible device 100 with a sheath 210 extending over the support structure 118. The sheath may abut or be coupled at a distal end to the distal mount 104. The sheath 210 may be braided, woven, coiled, or of another structure that flexibly bends with the support structure 118 while preventing a jacket 212 from buckling inward during bending and getting pinched between the links. The sheath 210 may also restrain the articulation members or other components of the articulation portion from protruding outward between the links. The sheath may be formed, for example, of metal or polymer fibers. In some examples of the flexible device, the sheath may be omitted.

Figure 5:
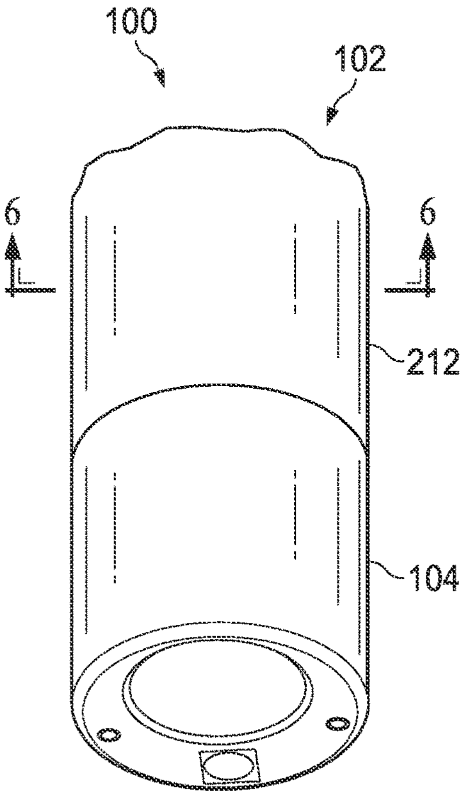
FIG. 5 illustrates the distal end of the elongated flexible device of FIG. 4 with an outer jacket.

FIG. 5 illustrates a distal end of the elongate flexible device 100 with a jacket 212 extending over the sheath 210. The jacket may abut or be coupled at a distal end to the distal mount 104. The jacket 212 may be formed of a flexible barrier material, such as a polymer, that flexibly bends with the support structure while resisting ingress of fluids and debris into the support structure 118.

FIG. 6 illustrates a cross-sectional view of the articulation portion 102. As shown, the jacket 212, sheath 210, links of support structure 118, and liner 108 may be generally concentric about the longitudinal axis A1. The support structure 118 may have an inner diameter D1 and an outer diameter D2. In addition to grooves 204 to accommodate the spring members 140, 142, 144, 146, the liner 108 may also include a groove 214 to accommodate an optical fiber shape sensor 216 and grooves 218 to accommodate illumination optical fibers 220. The liner 108 may also include a groove 222 to accommodate and guide one or more components, such as cables, of an imaging system 224. In this example the liner 108 occupies the space between the working lumen 110 and the inner diameter of the support structure 118, preventing migration of the sensor, illumination, and imaging components from their locations within the support structure 118.

A wall dimension of the articulation portion 102 may be minimized to maintain the size of the working lumen while minimizing the diameter of the flexible device 100. In some examples, an overall wall dimension D3 from the inner wall of the liner 108 to the outer surface of the jacket 212 may be approximately 0.026 inches. This may allow for an inner diameter D4 of approximately 0.085 inches, a spring member diameter of approximately 0.014 inches, a sheath thickness of approximately 0.002 inches, and a jacket thickness of approximately 0.003 inches.

Generally, a small overall wall dimension while maintaining an inner diameter D4 of a size sufficient (e.g., may be approximately 2.0 mm) to pass standard sized instruments may allow for a smaller total diameter D5 (e.g., may be less than or equal to approximately 3.5 mm) of the flexible device, allowing the device to pass into smaller anatomical passageways. A reduced diameter D5 may decrease bending stiffness by reducing the moment of inertia. A bending moment arm M1 between an outer edge of the spring pair 140, 142 and the center of the spring member 144 (or spring member 146) may be increased as compared to examples in which the spring member is affixed to the inner diameter of the link. For a given overall bending stiffness of articulation joint 122, the larger bending moment arm M1 reduces the required articulation forces on the articulation members to produce bending.

As compared to composite architectures that have spring members welded to the inner diameter of ring-shaped links, the design of the articulation portion 102 may provide one or more clinical benefits. For example, the articulation portion 102 may have a lower bending stiffness as compared to composite architectures that include a circumferentially continuous ring. By positioning the spring members between segments of the link wall, the moment bending arm may be increased thus requiring lower articulation forces on the articulation members to bend the articulation portion 102. Because the spring members may have a high degree of effective strain, a tight bend radius may be formed. Without support structure or other polymer material extending between levels of links, bulging of such material and occlusion of the inner diameter of the links may be reduced.

Figure 7:
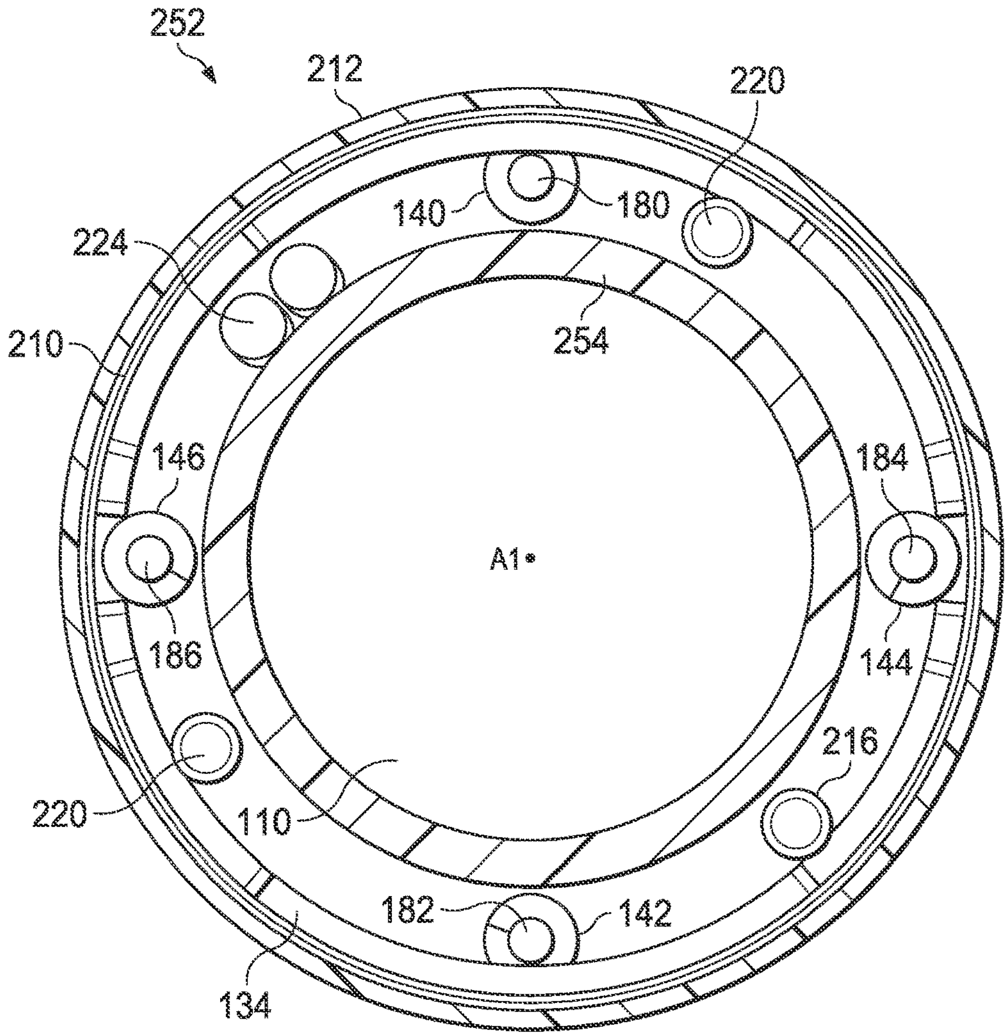
FIG. 7 illustrates a cross-sectional view of an articulation joint, according to some examples.

FIG. 7 illustrates a cross-sectional view of an articulation portion 252 according to an alternative example. In this example a liner 254 forms a working lumen 256 but has an outer diameter that extends only to the outer diameter of the spring members. In this example, grooves may be omitted from an outer surface of the liner 254 because the liner does not extend around the spring members or around the other sensing, illumination, or imaging components. The liner 254 may be similar to the liner 108 in other respects. With a thinner liner 254 (as compared to the liner 108) the liner may provide more flexibility. Liner 254 may be made from a composite material such as a braid reinforced plastic or coil reinforced plastic.

Figure 8:
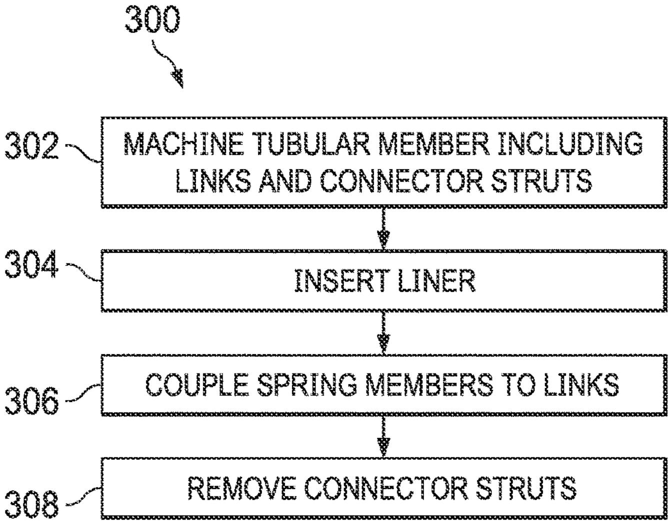
FIG. 8 is a flowchart illustrating a method for forming a support structure, according to some examples.

FIG. 8 is a flow chart illustrating a method 300 for creating a support structure (e.g., support structure 118). The method 300 is illustrated as a set of operations or processes. The processes illustrated in FIG. 8 may be performed in a different order than the order shown in FIG. 8, and one or more of the illustrated processes might not be performed in some embodiments of method 300. Additionally, one or more processes that are not expressly illustrated in FIG. 8 may be included before, after, in between, or as part of the illustrated processes. In some embodiments, one or more of the processes of method 300 may be implemented, at least in part, in the form of executable code stored on non-transitory, tangible, machine-readable media that when run by one or more processors (e.g., the processors of a machining system) may cause the one or more processors to perform one or more of the processes.

Figure 10:
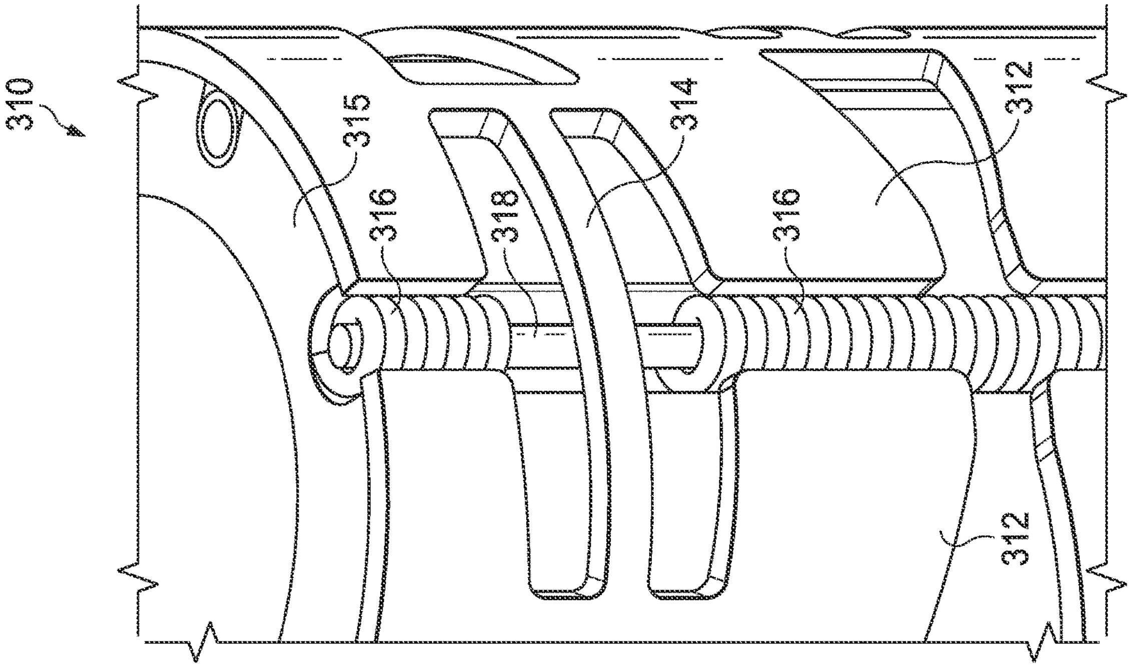
FIGS. 9 and 10 illustrate a portion of an articulation joint with a strut between links during an assembly process, according to some examples.
Figure 9:
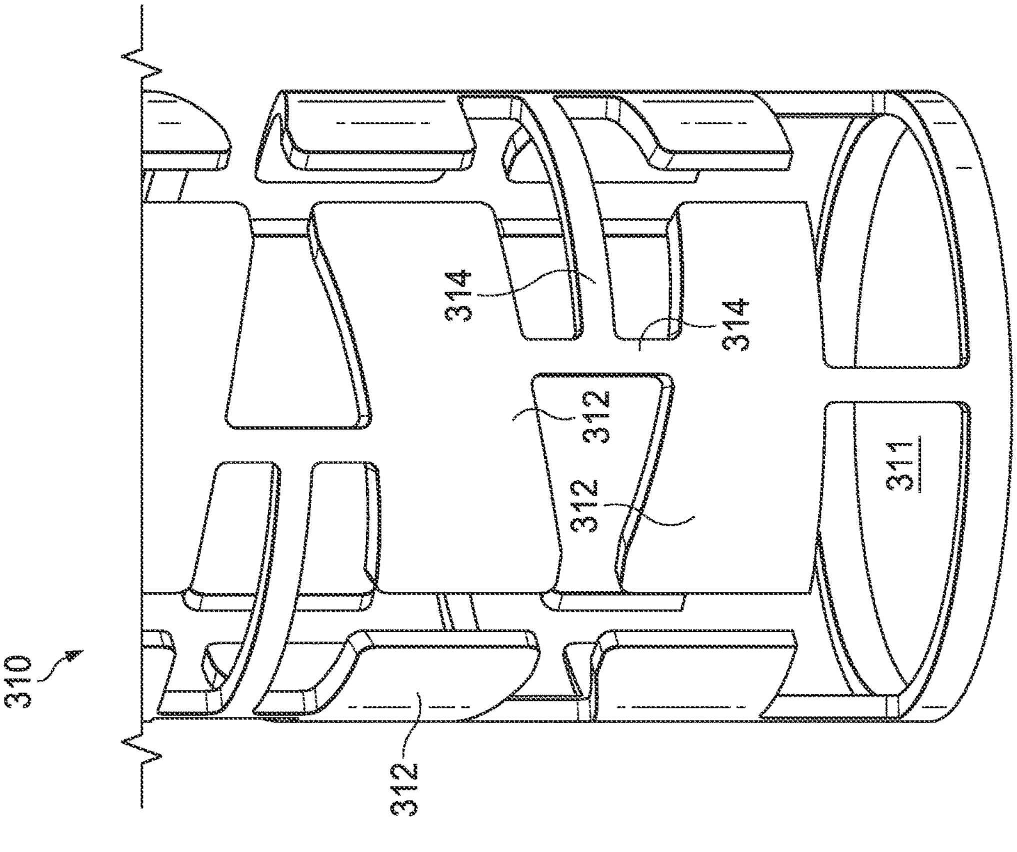

At a process 302 and with reference to FIGS. 9 and 10, a tubular member 310 with a lumen 311 (e.g., a stainless steel hypotube) may be machined to include a plurality of links 312 (e.g., links 120) and connector struts 314. The connector struts 314 are not part of the articulation joint in use, but rather these are temporary struts which may be included as a manufacturing aid to hold the links aligned until the spring members are attached. At a process 304, a tool 315 with slots for the springs (e.g., with similar profile to liner 108) may be inserted into the lumen 311 of the tubular member 310. At a process 306, a spring member 316 (e.g., spring members 140, 142, 144, 146) may be laser welded or otherwise affixed to the links such that the spring member 316 extends into the lumen 311 of the tubular member without protruding past the outer diameter of the tubular member 310. With the connector struts 314 in place while the spring members 316 are affixed to the links 312, the struts provide rigidity and maintain link positions. Articulation member 318 or a tool of similar size may extend through the spring member 316 to ensure alignment while affixing to the links. At a process 308, the connector struts 314 may be removed (e.g., cut or snapped out) from between the links 312. With the connector struts 314 removed, the spring members 316 and the articulation members 318 provide the connective structure between the links 312 and permit bending of the joints.

Figure 11:
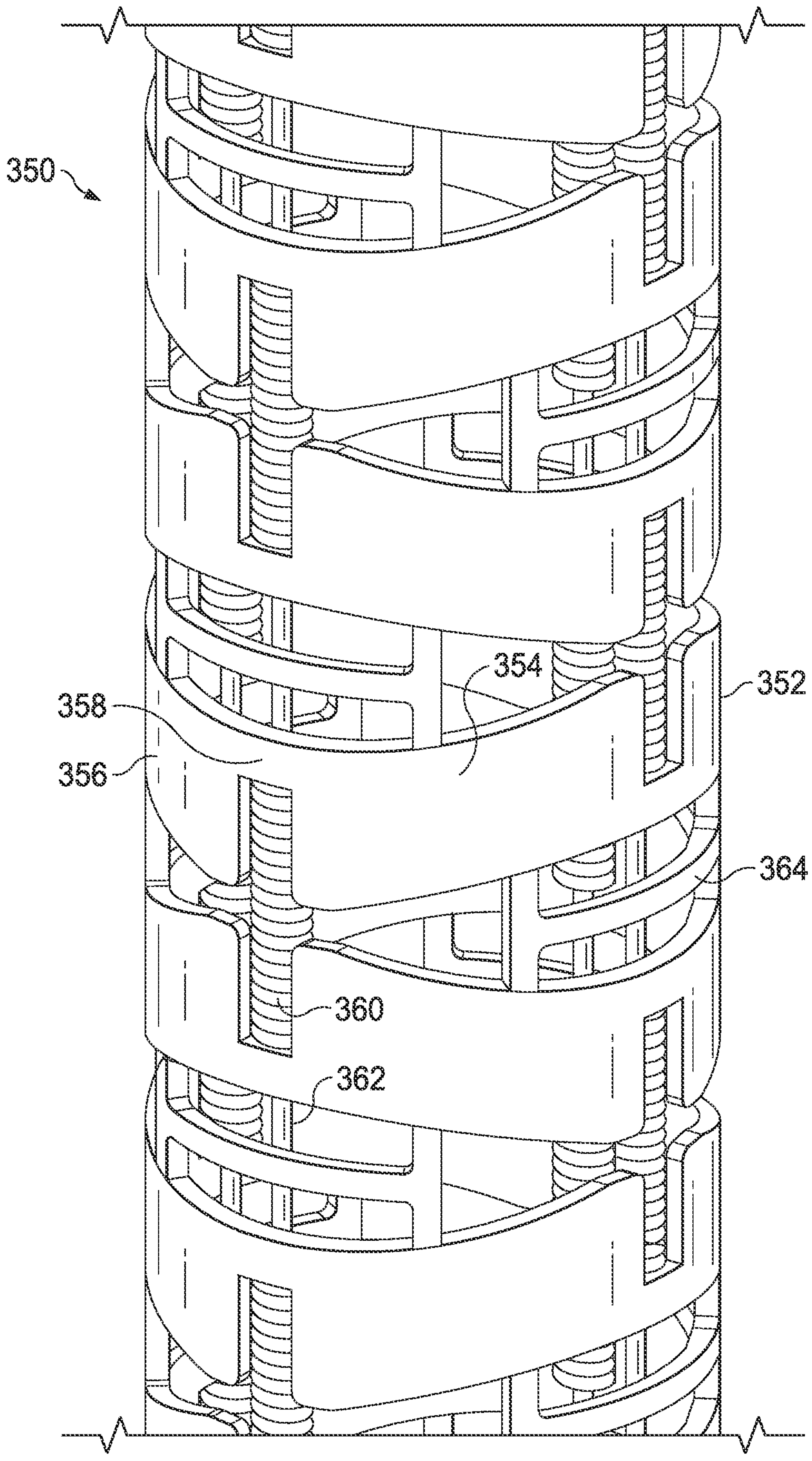
FIG. 11 illustrates a portion of an articulation joint, according to some examples.

FIG. 11 illustrates a support structure 350 that may be substantially similar to support structure 118 with the differences as described. In this example, link 352 may be circumferentially contiguous with arcuate segments 354, 356 of the link 352 coupled by a bridge section 358 that also provides end support for a spring member 360. In this example, the spring members may be affixed (e.g., laser welded) to the bridge sections and/or the links. The bridge section 358 may provide additional support for the spring member and may provide additional axial stiffness to the overall support structure 350 to prevent compression. An additional effect of this design may be to reduce the need for a tightly toleranced manufacturing fixture to axially locate the springs. Due to the material of bridge section 358, the springs may not extend into or out of their respective locations. In this example, the spring member 360 may be flush or recessed with respect to the outer diameter of the support structure such that the articulation member 362 that extends through the spring member extends within the inner diameter of the support structure 350. In the example shown in FIG. 11, the connector struts 364 may be removed after the spring members 360 are coupled to the links.

Figure 12:
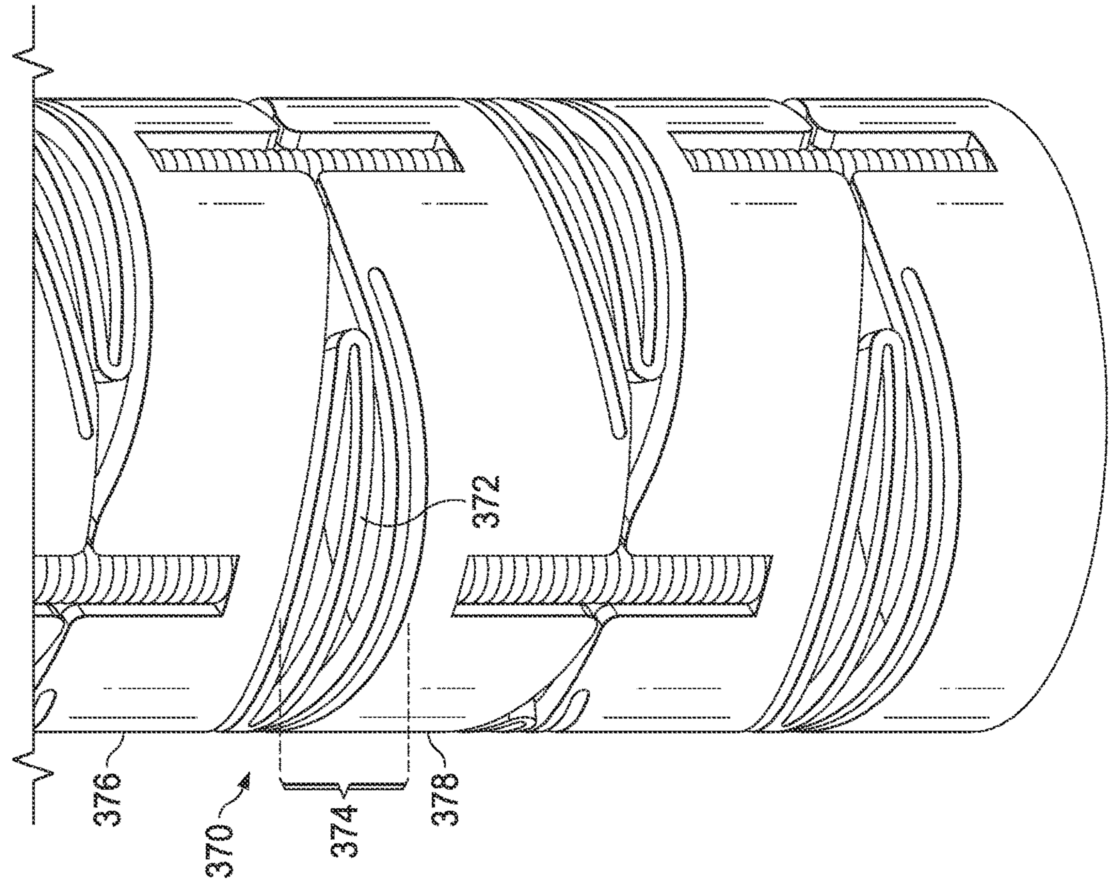
FIG. 12 illustrates a portion of an articulation joint with a flexible lattice between links, according to some examples.

FIG. 12 illustrates a support structure 370 that may be substantially similar to support structure 350 with the differences as described. In this example, a flexible lattice structure 372 may extend across a bending gap 374 between links 376 and 378. The lattice structure 372 may flex open or close as the support structure 370 bends. As compared to an open, unobstructed, bending gap as in prior examples, the lattice structure 372 may resist ingress of the jacket structure 212 into the bending gap and may eliminate the need for sheath 210. Whereas support structure 350 is removed on completion of the manufacturing process to allow bending of the links, support structure 370 may not need to be removed because it does not inhibit bending and so may eliminate a manufacturing step.

Figure 13:
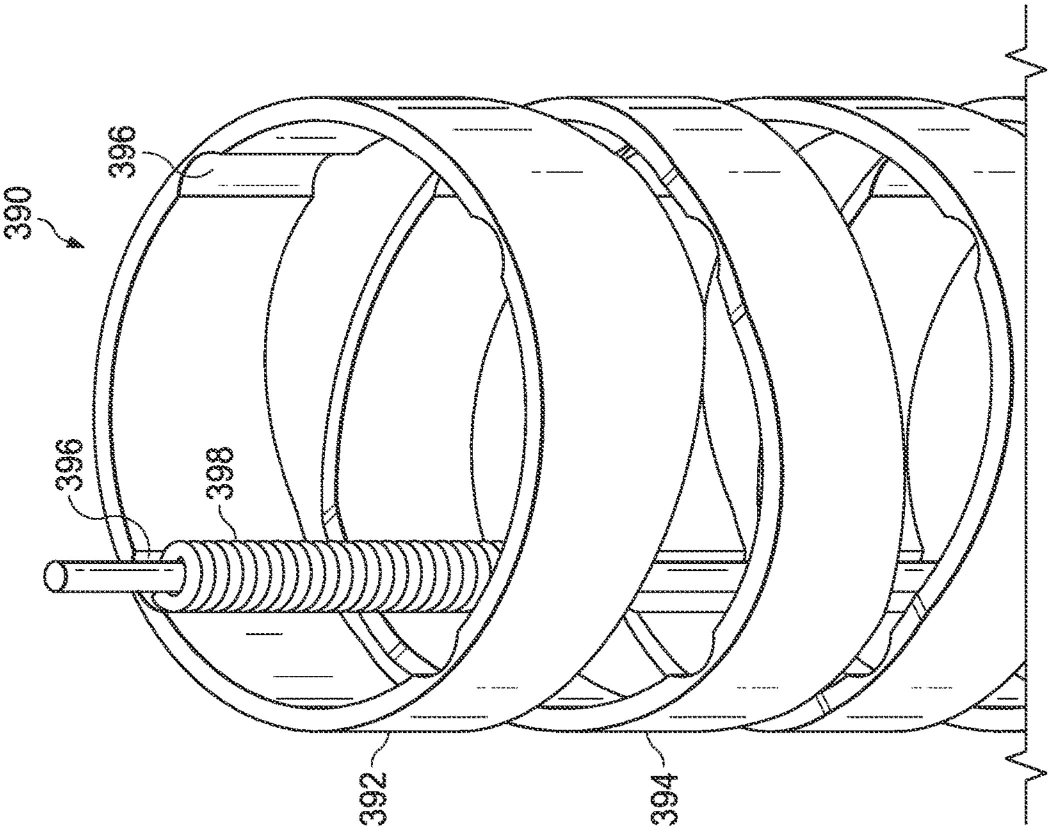
FIG. 13 illustrates a portion of an articulation joint with grooves in the interior wall, according to some examples.

FIG. 13 illustrates a support structure 390 that may be substantially similar to support structure 118 with the differences as described. In this example, the support structure 390 is formed of links, including links 392, 394, that may be circumferentially contiguous, ring-like structures that include grooves 396 along an inner surface of the links. The groove 396 may serve to positively locate a spring member 398 and serve as an attachment point for coupling (e.g., laser welding) the spring member 398 to the inner surface of the link 392.

Figure 14:
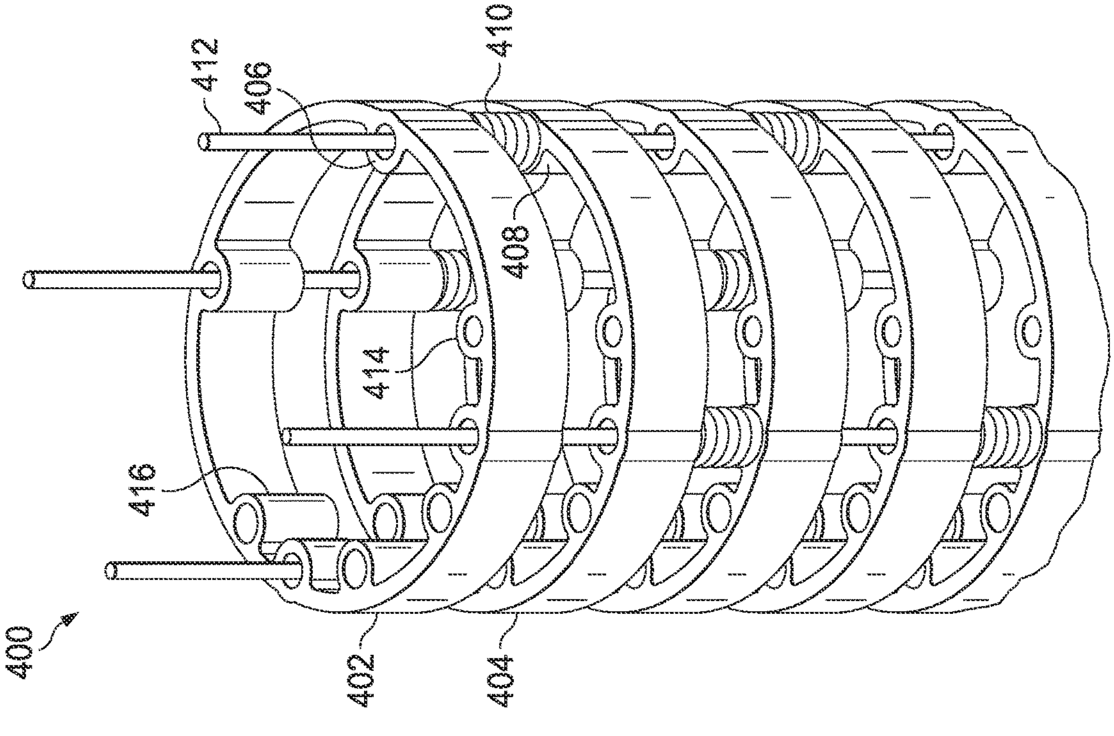
FIG. 14 illustrates a portion of an articulation joint with conduits coupled to the interior of the walls, according to some examples.

FIG. 14 illustrates a support structure 400 that may be substantially similar to support structure 118 with the differences as described. In this example, the support structure 400 is formed of links of varying wall thickness, including links 402, 404, that may be circumferentially contiguous, ring-like structures. In this example, the link 402 is thicker in at least two locations to include a plurality of conduits integrally formed with an inner surface of the link. For example, a conduit 406 may be integrally formed with the inner surface of the link 402, and a conduit 408 may be integrally formed with the inner surface of the link 404. Links 402 and 404 may have significantly thinner walls between the conduits to allow space for additional components. An end portion of a spring member 410 may be coupled to (e.g., laser welded) to a bottom portion of the conduit 406 and to a top portion of the conduit 408 such that the passages through the conduits 406, 408 and the spring member 410 are generally aligned to allow passage of an articulation member 412. Other conduits 414, 416 may be sized and shaped to allow passage of other components including imaging, irrigation, illumination, sensing or other systems. Alternatively, there may be no additional conduits and these other components may occupy the space between the articulation conduits, bounded on the outside by the thinner wall of the link and constrained on the inside by a liner 254 as shown in FIG. 7.

Figure 15:
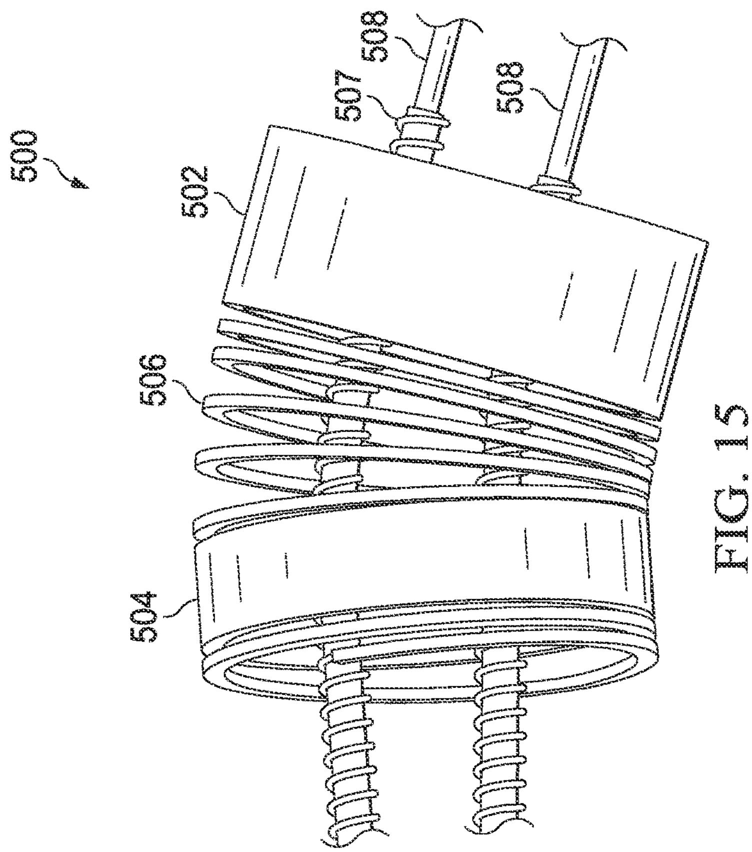
FIG. 15 illustrates a portion of an articulation joint with a helical coil, according to some examples.

FIG. 15 illustrates a support structure 500 including links 502, 504 coupled by a helical coil 506. In this example, a spring member 507 (e.g., substantially similar to spring member 140) may be coupled to (e.g., laser welded) to the inner walls of the links 502, 504 to provide a conduit for an articulation member 508 and to provide additional axial support to the support structure 500. In some examples the links 502, 504 may be circumferentially continuous rings, and in some examples the links may be tightly-closed coils or welded-tight coils. In some examples, the helical coil 506 and the links 502, 504 may be integrally formed from a single hypotube. In other examples, the helical coil 506 may be welded or otherwise coupled to the links 502, 504.

Figure 16A:
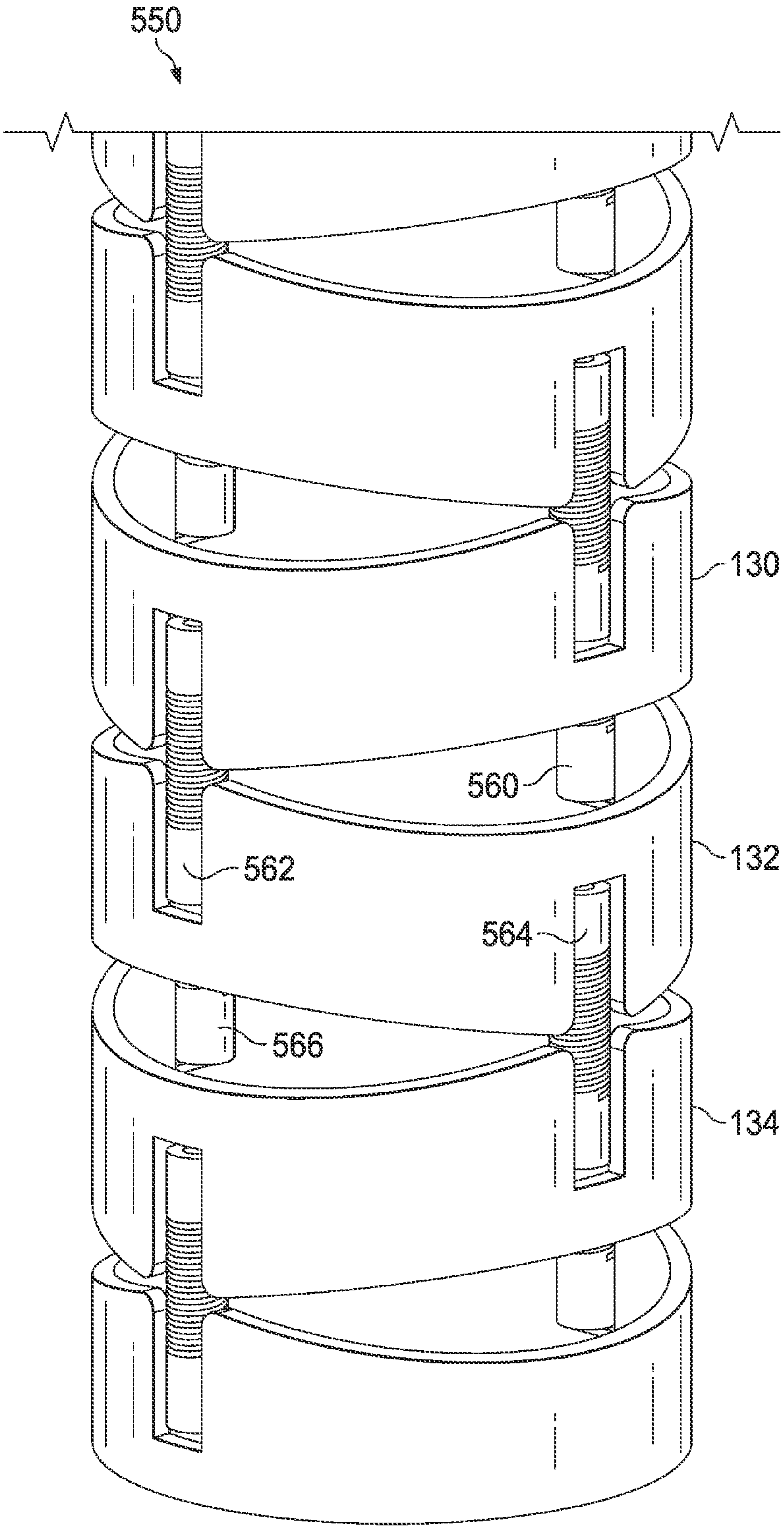
FIG. 16A illustrates a portion of an articulation joint, according to some examples.
Figure 16B:
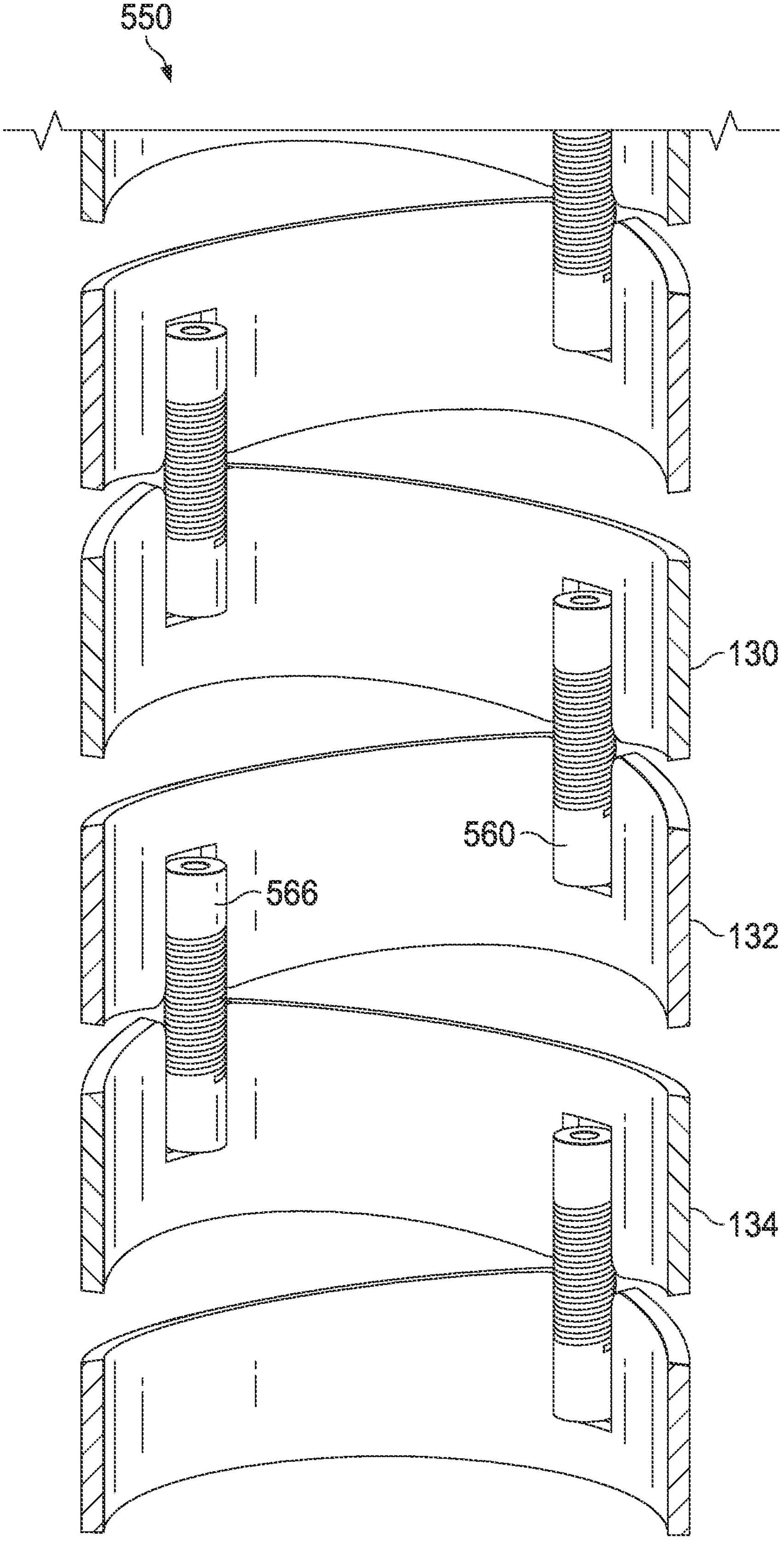
FIG. 16B illustrates a cross sectional view of the portion of the articulation joint of FIG. 16A.

FIG. 16A illustrates a portion of an articulation joint 550, and FIG. 16B illustrates a cross sectional view of the portion of the articulation joint 550. The articulation joint 550 may be substantially similar to the articulation joint 122 with the differences as described. The articulation joint 550 includes link 130, link 132, and link 134 arranged in series. The articulation joint 550 also includes paired spring members 560, 562 extending between paired links 130, 132 and paired spring members 564, 566 extending between paired links 132, 134. In this example, the spring members 560-566 may be formed from a hypotube with a laser-cut helical pattern. The helical cut may allow the spring member to bend and flex to generate the same bending of the joint 550 as described in FIGS. 2B and 2C.

Figure 17:
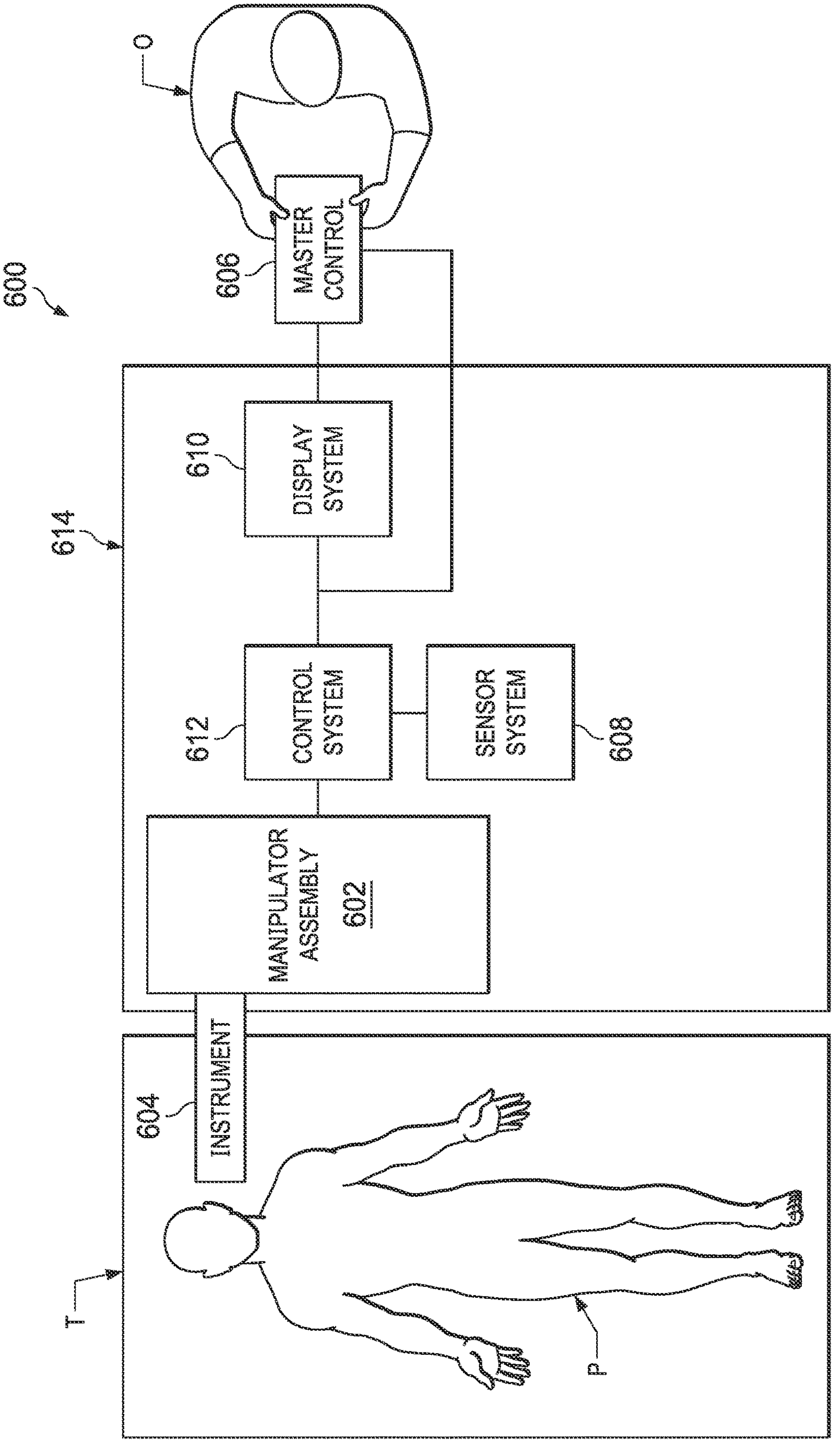
FIG. 17 is a simplified diagram of a medical system configured in accordance with some examples.
Figure 18:
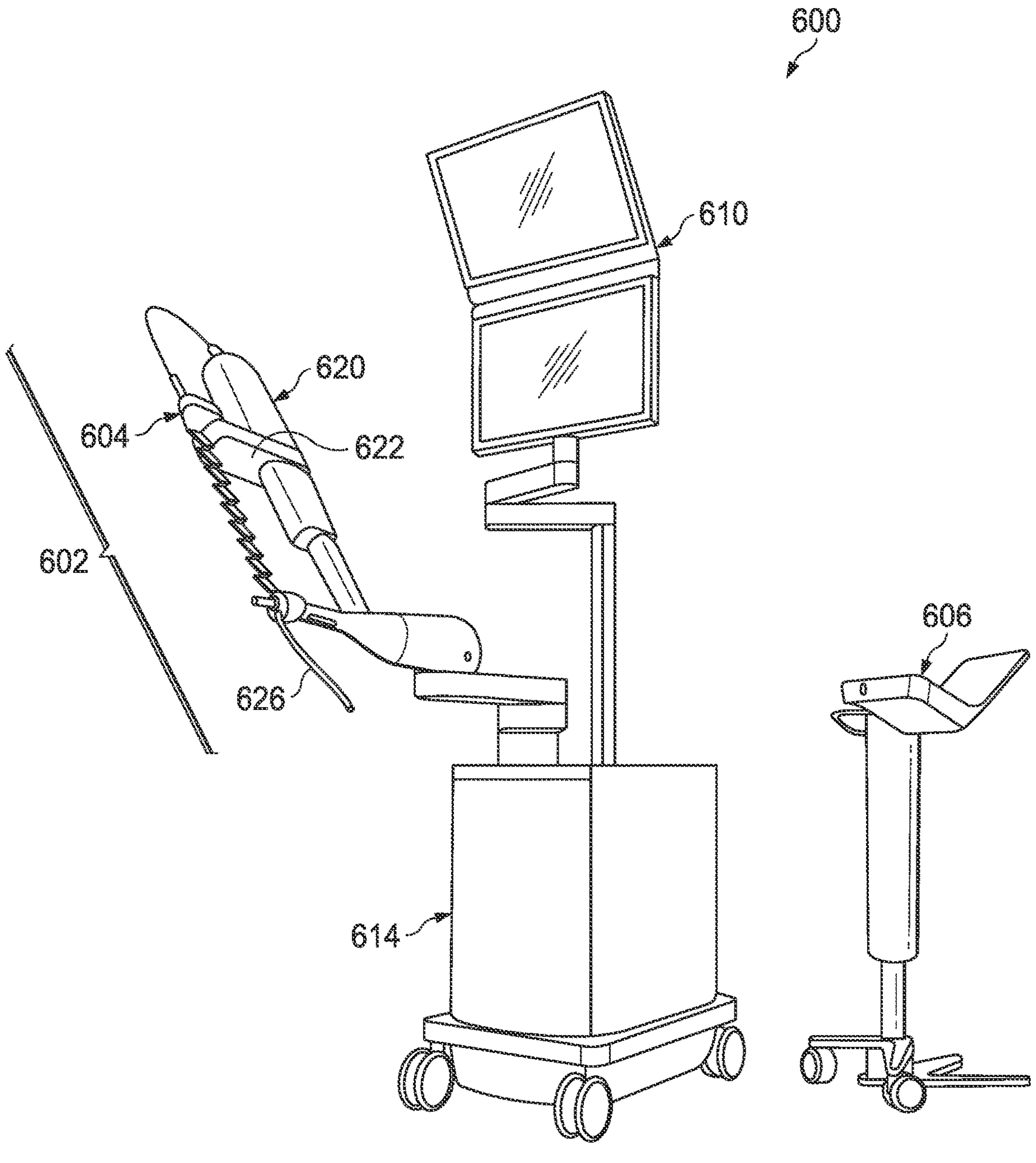
FIG. 18 is a perspective view of a structural representation of the medical system of FIG. 17.

The elongate flexible devices and support structures described herein may be used within various systems, including a medical system. FIG. 17 is a simplified diagram of a medical system 600 and FIG. 18 is a perspective view of the system 600 configured in accordance with embodiments of the present technology. The system 600 may be suitable for use in surgical, diagnostic, therapeutic, or biopsy procedures, among others. While some embodiments of the system 600 are described herein with respect to such procedures, references to specific medical or surgical instruments and medical or surgical methods is not intended to limit the scope of the present technology. The systems, instruments, and methods described herein may be used for humans, animals, human cadavers, animal cadavers, portions of human or animal anatomy, and/or non-surgical diagnosis, as well as industrial systems and general robotic or teleoperational systems.

As shown in FIGS. 17 and 18, the system 600 generally includes a manipulator assembly 602 having an instrument manipulator 620 (see FIG. 18) to manipulate a medical instrument 604 including an elongate device 626 (e.g. the flexible device 100) while performing various procedures on a patient P. The optical fiber alignment assemblies described herein may be used to align, couple, and/or clean optical fibers in the instrument manipulator 620 and the medical instrument 604, as previously described. The manipulator assembly 602 may be teleoperated, non-teleoperated, or a hybrid teleoperated and non-teleoperated assembly with select degrees of freedom of motion that may be motorized and/or teleoperated, and select degrees of freedom of motion that may be non-motorized and/or non-teleoperated. The manipulator assembly 602 may be mounted to an operating table T, or to a main support 614 (e.g. a movable cart, stand, second table, etc.). The system may include a master control 606 configured to allow an operator O (e.g., a surgeon, clinician, physician, etc.) to view the interventional site and to control the manipulator assembly 602.

The master control 606 of the system 600 may be located near or in the same room as the operating table T. In some embodiments, for example, the master control 606 is positioned near the side of a surgical table T on which the patient P is located. However, it should be understood that the operator O can be located in a different room or any distance away from the patient P. The master control 606 generally includes one or more input and control devices (not shown) for controlling the medical instrument 604 via the instrument manipulator 620. The input and control devices may include any number of a variety of input devices, such as joysticks, trackballs, data gloves, trigger-guns, hand-operated controllers, voice recognition devices, body motion or presence sensors, etc. The input and control devices may be provided with the same degrees of freedom as the associated medical instrument to take advantage of the familiarity of the operator O in directly controlling like instruments. In this regard, the control devices may provide operator O with telepresence or the perception that the control devices are integral with the medical instruments. However, the input and control devices may have more or fewer degrees of freedom than the associated medical instrument 604 and still provide operator O with telepresence. In some embodiments, the control devices may optionally be manual input devices that move with six degrees of freedom, and which may also include an actuatable handle for actuating instruments (e.g., for closing grasping jaws, applying an electrical potential to an electrode, delivering a medicinal treatment, etc.).

The input and control devices of the master control 606 may include a scroll wheel and a trackball. In an example implementation of the system 600, the scroll wheel may be rolled forwards or backwards in order to control the advancement or retraction of the medical instrument 604 with respect to the patient anatomy, and the trackball may be rolled in various directions by the operator O to steer the position of the distal end portion and/or distal tip of the medical instrument 604, e.g., to control bend or articulation. Various systems and methods related to motion control consoles are described in PCT Pub. No. 2019/027922 (filed Jul. 30, 2018, titled "Systems and Methods for Safe Operation of a Device"), and U.S. Patent Pub. No. 2019/0029770 (filed Jul. 30, 2018, titled "Systems and Methods for Steerable Elongate Device"), which are incorporated by reference herein in their entireties.

As shown in FIG. 18, the instrument manipulator 620 may be configured to support and manipulate the medical instrument 604 with a kinematic structure of one or more non-servo-controlled links (e.g., one or more links that may be manually positioned and locked in place, generally referred to as a set-up structure (SUS)), and/or one or more servo-controlled links (e.g., one or more powered links that may be controlled in response to commands). The instrument manipulator 620 may include a plurality of actuators or motors that drive inputs on the medical instrument 604 in response to commands from a control system 612. The actuators may include drive systems that when coupled to the medical instrument 604 may advance the medical instrument 604 into a naturally or surgically created anatomic orifice in the patient P. In some embodiments, the kinematic structure may be locked in place or unlocked to be manually manipulated by the operator O interacting with switches, buttons, or other types of input devices.

The instrument manipulator 620 may be configured to position the medical instrument 604 at an optimal position and orientation relative to patient anatomy or other medical devices. In this regard, drive systems may be included in the instrument manipulator 620 to move the distal end of the medical instrument 604 according to any intended degree of freedom, which may include three degrees of linear motion (e.g., linear motion along the X, Y, and/or Z Cartesian axes) and three degrees of rotational motion (e.g., rotation about the X, Y, and Z Cartesian axes). Additionally, the actuators can be used to actuate an articulable end effector (not shown) of the medical instrument 604 for grasping tissue in the jaws of a biopsy device or the like. Actuator position sensors, such as resolvers, encoders, potentiometers, and other mechanisms, may provide sensor data to the system 600 describing the rotation and orientation of the motor shafts of the instrument manipulator 620. Such position sensor data may be used to determine motion of the objects manipulated by the actuators.

In some embodiments, the optimal location and orientation can include alignment of the manipulator assembly 602 with respect to anatomy of the patient P, for example, to minimize friction of the medical instrument 604 positioned within the anatomy of the patient P (e.g. in anatomical openings, patient vasculature, patient endoluminal passageways, etc.), or within medical devices coupled to patient anatomy (e.g. cannulas, trocars, endotracheal tubes (ETT), laryngeal esophageal masks (LMA), etc.). Optimal location and orientation of the manipulator assembly 602 can additionally or alternatively include optimizing the ergonomics for the operator O by providing sufficient workspace and/or ergonomic access to the medical instrument 604 when utilizing various medical tools such as needles, graspers, scalpels, grippers, ablation probes, visualization probes, etc. with the medical instrument 604.

Each adjustment of the manipulator assembly 602 (e.g., insertion, rotation, translation, etc.) can be actuated by either robotic control or by manual intervention by the operator O. For example, each rotational or linear adjustment may be maintained in a stationary configuration using brakes. In this regard, depression of one or more buttons and switches releases one or more corresponding brakes, allowing the operator O to manually position the medical instrument 604 through positioning of the instrument manipulator 620. One or more adjustments may also be controlled by one or more actuators (e.g., motors) such that an operator may use a button or switch to actuate a motor to alter the manipulator assembly 602 in a desired manner to position the manipulator assembly 602 in the optimal position and orientation. In some embodiments, robotic control of the manipulator assembly 602 can be actuated by activating a button or switch. In one example, one position of the button or switch may initiate powered rotation of the manipulator assembly 602 in a first direction of rotation and another position of the button or switch may initiate powered rotation of the manipulator assembly 602 in the other direction.

The manipulator assembly 602 may be configured such that when a button or switch is activated, the operator O may adjust the instrument manipulator 620 along a linear path that corresponds to inserting or retracting the medical instrument 604. For safety purposes, the manipulator assembly 602 might only be manually movable in one translation direction, such as retraction, and might not be manually movable in the direction of insertion of the medical instrument 604, to prevent the operator O from inadvertently or undesirably advancing the medical instrument into the anatomy of the patient O.

As shown in FIG. 17, the system 600 may include a sensor system 608 with one or more sub-systems for receiving information about the instruments coupled to the instrument manipulator 620. Such sub-systems may include a position/location sensor system (e.g., an electromagnetic (EM) sensor system); a shape sensor system (e.g., an optical fiber shape sensor) for determining the position, orientation, speed, velocity, pose, and/or shape of a distal end, and/or of one or more segments along a flexible body that may make up a portion of the medical instrument 604; and/or a visualization system for capturing images from the distal portion of the medical instrument 604, among other possible sensors.

Referring again to FIGS. 17 and 18 together, the system 600 also may include a display system 610 for displaying an image or representation of the surgical site and the medical instrument 604 generated the sensor system 608, recorded pre-operatively or intra-operatively. The display system 610 may use image data from imaging technology and/or a real time image, such as by computed tomography (CT), magnetic resonance imaging (MRI), fluoroscopy, thermography, ultrasound, optical coherence tomography (OCT), thermal imaging, impedance imaging, laser imaging, nanotube X-ray imaging, endoscopic images, and the like, or combinations thereof. The pre-operative or intra-operative image data may be presented as two-dimensional, three-dimensional, or four-dimensional (including e.g., time based or velocity-based information) images and/or as images from models created from the pre-operative or intra-operative image data sets. The display system 610 and the master control 606 may be oriented such that the operator O can control the medical instrument 604 and the master control 606 with the perception of telepresence.

The display of visual indicators, markers, and or images on the display system 610 may be altered by input devices (e.g., buttons, switches, etc.) on the manipulator assembly 602 and/or the master control 606. For example, actuating button or switch can cause a marker to be placed in a rendered model of patient anatomy displayed on the display system 610. The marker could correspond to an area within the patient at which a procedure (e.g., biopsy) has been performed, or otherwise indicate an actual location within the patient anatomy where the medical instrument has been positioned. Such a virtual navigational marker may be dynamically referenced with registered preoperative or concurrent images or models. Systems and methods for registration are provided in PCT Pub. No. WO 2016/191298 (published Dec. 1, 2016, titled "Systems and Methods of Registration for Image Guided Surgery"), and in U.S. Pat. No. 8,900,131 (filed May 13, 2011, titled "Medical System Providing Dynamic Registration of a Model of an Anatomic Structure for Image-Guided Surgery"), which are incorporated by reference herein in their entireties.

The control system 612 may include at least one memory and at least one computer processor (not shown) for effecting control between the medical instrument 604, the master control 606, the sensor system 608, and the display system 610. The control system 612 may also include programmed instructions, which may be stored on a non-transitory machine-readable medium, to implement some or all of the methods described in accordance with aspects of the present technology disclosed herein, including instructions for providing information to the display system 610. The control system 612 may include two or more data processing circuits with one portion of the processing optionally being performed on or adjacent to the manipulator assembly 602, another portion of the processing being performed at the master control 606, etc. The processors of the control system 612 may execute instructions for the processes disclosed herein. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, the control system 612 supports wireless communication protocols, such as Bluetooth, IrDA, HomeRF, IEEE 802.11, DECT, Wireless Telemetry, and the like.

The control system 612 may receive force and/or torque feedback from the medical instrument 604. In response, the control system 612 may transmit signals to the master control 606. In some embodiments, the control system 612 may transmit signals instructing one or more actuators of the manipulator assembly 602 to move the medical instrument 604. The medical instrument 604 may extend into an internal surgical site within the body of patient P via openings in the body of patient P. Any suitable conventional and/or specialized actuators may be used with the manipulator assembly 602. The one or more actuators may be separate from, or integrated with, the manipulator assembly 602. In some embodiments, the one or more actuators and the manipulator assembly 602 are provided as part of the main support 614, which can be positioned adjacent to the patient P and the operating table T. In some embodiments, the manipulator assembly 602, control system 612, sensor system 608, and display system 610 may be supported by the main support 614, or some or all of these components may be integrated into the main support 614. Alternatively, one or more of these components may be mounted to the operating table T or integrated into the master control 606.

The control system 612 may further include a virtual visualization system to provide navigation assistance to the operator O when controlling the medical instrument 604 during an image-guided surgical procedure. Virtual navigation using the virtual visualization system may be based upon reference to an acquired preoperative or intraoperative dataset of anatomic passageways. During a virtual navigation procedure, the sensor system 608 may be used to compute an approximate location of the medical instrument 604 with respect to the anatomy of the patient P. The location can be used to produce both macro-level tracking images (external to the anatomy of patient P) and virtual images (internal to the anatomy of patient P). The control system 612 may implement one or more EM sensor, fiber optic sensors, and/or other sensors to register and display a medical implement together with preoperatively recorded surgical images, such as those from a virtual visualization system. For example, PCT Pub. No. WO 2016/191298 (published Dec. 1, 2016, titled "Systems and Methods of Registration for Image Guided Surgery"), which is incorporated by reference herein in its entirety, discloses one such system. Various systems and methods for monitoring the shape and relative position of an optical fiber in three dimensions are described in U.S. Pat. No. 7,781,724 (filed Sep. 26, 2006, titled "Fiber Optic Position and Shape Sensing Device and Method Relating Thereto"); U.S. Pat. No. 7,772,541 (filed on Mar. 12, 2008, titled "Fiber Optic Position and/or Shape Sensing Based on Rayleigh Scatter"); and U.S. Pat. No. 6,389,187 (filed on Jun. 17, 1998, titled "Optical Fiber Bend Sensor"), which are all incorporated by reference herein in their entireties.

The system 600 may further include optional operations and support systems (not shown) such as illumination systems, steering control systems, irrigation systems, and/or suction systems. In some embodiments, the system 600 may include more than one manipulator assembly and/or more than one master control. The exact number of teleoperational manipulator assemblies can be tailored for the surgical procedure to be performed and/or the space constraints within the operating room, among other factors. Multiple master controls may be collocated or positioned in separate locations. Multiple master controls allow more than one operator to control one or more teleoperational manipulator assemblies in various combinations.

The instrument manipulator 620 can be configured to support and position an elongate device 626 (e.g., device 100) of the medical instrument 604. Various elongate devices are described in PCT Pub. No. WO 2019/018736 (filed Jul. 20, 2018, titled "Flexible Elongate Device Systems and Methods"), which is incorporated by reference herein in its entirety.

The system 600 may be configured to allow positioning of the display system 610 and main support 614 at a desired location relative to the operating table T and the patient P. Various systems and methods relating to a display system and a main support are described in PCT Pub. No. WO 2018/132386 (filed Jan. 9, 2018, titled "Systems and Methods for Using a Robotic Medical System"), which is incorporated by reference herein in its entirety. The main support 614 may include hardware (e.g., processor(s), firmware, etc.) and/or or software to perform functions for performing shape-sensing with respect to a flexible elongate device.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. Not all the illustrated processes may be performed in all embodiments of the disclosed methods. Additionally, one or more processes that are not expressly illustrated in may be included before, after, in between, or as part of the illustrated processes. In some embodiments, one or more of the processes may be performed by a control system or may be implemented, at least in part, in the form of executable code stored on non-transitory, tangible, machine-readable media that when run by one or more processors may cause the one or more processors to perform one or more of the processes.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for imaging, via natural or surgically created connected passageways, in any of a variety of anatomic systems, including the lung, colon, the intestines, the stomach, the liver, the kidneys and kidney calices, the brain, the heart, the circulatory system including vasculature, and/or the like. While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Note that the processes and displays presented might not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

This disclosure describes various instruments, portions of instruments, and anatomic structures in terms of their state in three-dimensional space. As used herein, the term position refers to the location of an object or a portion of an object in a three-dimensional space (e.g., three degrees of translational freedom along Cartesian x-, y-, and z-coordinates). As used herein, the term orientation refers to the rotational placement of an object or a portion of an object (e.g., in one or more degrees of rotational freedom such as roll, pitch, and/or yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

While certain illustrative embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A catheter system comprising:

an articulation joint including a first pair of links and a second pair of links, each link including a central channel enclosed at least in part by radially extending arcuate segments, wherein the first pair of links includes a first link and a second link, and the second pair of links includes the second link and a third link;

a tubular liner extending through the central channel, wherein the tubular liner includes an outer surface including a groove sized to receive at least one of an imaging component, a sensor, an illumination component, or an irrigation component;

a first pair of springs coupled between the first and second links and extending between a pair of the arcuate segments of the first link and a first pair of the arcuate segments of the second link;

a second pair of springs coupled between the second and third links and extending between a second pair of the arcuate segments of the second link and a pair of the arcuate segments of the third link, wherein the second pair of springs is offset in angular position from the first pair of springs;

a first pair of control wires extending through the first pair of springs; and a second pair of control wires extending through the second pair of springs, wherein at least one spring of the first pair of springs has a spring wall and the first link includes a link wall and wherein the spring wall shares a radial dimension with the link wall.

2. The catheter system of claim 1, wherein the offset is 90°.

3. The catheter system of claim 1, wherein the at least one spring of the first pair of springs is welded between the pair of arcuate segments of the first link.

4. The catheter system of claim 1, wherein the at least one spring of the first pair of springs has a length that is equal to or greater than a height of the first link.

5. The catheter system of claim 1, wherein the at least one spring of the first pair of springs extends into a groove in the first link.

6. The catheter system of claim 1, wherein the first and second link are coupled by a lattice.

7. The catheter system of claim 1, wherein an outer diameter of one of the springs of the first pair of springs is tangential to an outer surface of the first link.

8. The catheter system of claim 1, wherein the link wall has a thickness that spans the radial dimension.

9. A catheter system comprising:
- an articulation joint including:
  - a first pair of links including a first link and a second link; and
  - a second pair of links including one of the first link or the second link of the first pair of links;
- a first spring coupled between a first pair of spaced apart segments of the first link and between a first pair of spaced apart arcuate segments of the second link, the first spring bendable to allow articulation of the first pair of links along a first plane of motion;
- a second spring coupled between a first pair of spaced apart segments of a first link of the second pair of links and between a first pair of spaced apart segments of a second link of the second pair of links, the second spring bendable to allow articulation of the second pair of links along a second plane of motion;
- a third spring coupled between a second pair of spaced apart segments of the first link of the second pair of links and between a second pair of spaced apart segments of the second link of the second pair of links, the third spring bendable to allow articulation of the second pair of links along the second plane of motion; and
- a control wire extending through the first spring.

10. The catheter system of claim 9, wherein the first pair of spaced apart segments of the first link includes arcuate segments.

11. The catheter system of claim 9, further comprising a fourth spring coupled between a second pair of spaced apart segments of the first link of the first pair of links and between a second pair of spaced apart segments of the second link of the first pair of links, the second spring bendable to allow articulation of the first pair of links along the first plane of motion.

12. The catheter system of claim 9, wherein the first and second planes of motion are perpendicular.

13. The catheter system of claim 9, wherein the first spring is welded between the first pair of spaced apart segments of the first link of the first pair of links.

14. The catheter system of claim 9, wherein an outer surface of the first spring is within an outer diameter of the first link of the first pair of links.

15. The catheter system of claim 9, wherein an outer surface of the first spring extends into a central passage bounded by an inner surface of the first link of the first pair of links.

16. The catheter system of claim 9, wherein an outer surface of the first spring extends to an outer diameter of the first link to maximize an inner lumen space of the first link.

17. The catheter system of claim 9, wherein a bridge extends between the first pair of spaced apart segments of the first link of the first pair of links and wherein the first spring includes an end portion engaged with the bridge.

18. The catheter system of claim 9, wherein a flexible lattice extends between the first and second links of the first pair of links.

19. The catheter system of claim 9, wherein the articulation joint is formed from a stainless steel hypotube.

20. The catheter system of claim 9, further comprising a braided sheath extending around the articulation joint.

21. The catheter system of claim 9, further comprising a flexible jacket extending around the articulation joint.

22. The catheter system of claim 9, further comprising a tubular liner extending through a central passage bounded by the articulation joint.

23. The catheter system of claim 22, wherein the tubular liner includes an inner layer of PTFE and an outer layer of expanded PTFE.

24. The catheter system of claim 22, wherein the tubular liner includes a central channel sized to slidably receive an instrument.

* * * * *